(12) United States Patent
Bebot

(10) Patent No.: US 8,940,283 B2
(45) Date of Patent: *Jan. 27, 2015

(54) COSMETIC COMPOSITION COMPRISING AT LEAST ONE CATIONIC POLY(VINYLLACTAM), AT LEAST ONE FATTY ALCOHOL, AND AT LEAST ONE POLYOL, COSMETIC PROCESS FOR TREATING KERATIN FIBERS AND USE OF THE COMPOSITION

(75) Inventor: Cecile Bebot, Asnieres (FR)

(73) Assignee: L'Oreal, Paris (FR)

( * ) Notice: Subject to any disclaimer, the term of this patent is extended or adjusted under 35 U.S.C. 154(b) by 1078 days.

This patent is subject to a terminal disclaimer.

(21) Appl. No.: 11/643,861

(22) Filed: Dec. 22, 2006

(65) Prior Publication Data

US 2007/0190015 A1 Aug. 16, 2007

Related U.S. Application Data

(60) Provisional application No. 60/761,331, filed on Jan. 24, 2006.

(30) Foreign Application Priority Data

Dec. 22, 2005 (FR) ...................................... 05 13195

(51) Int. Cl.
| | | |
|---|---|---|
| *A61K 8/58* | (2006.01) | |
| *A61K 8/34* | (2006.01) | |
| *A61Q 5/12* | (2006.01) | |
| *A61K 8/81* | (2006.01) | |

(52) U.S. Cl.
CPC ................ *A61K 8/817* (2013.01); *A61K 8/345* (2013.01); *A61K 8/342* (2013.01); *A61Q 5/12* (2013.01)
USPC .............. 424/70.121; 424/70.17; 424/70.122; 424/70.15; 424/70.12; 222/394

(58) Field of Classification Search
CPC ....... A61K 8/342; A61K 8/345; A61K 8/817; A61Q 5/12
See application file for complete search history.

(56) References Cited

U.S. PATENT DOCUMENTS

| | | | | |
|---|---|---|---|---|
| 4,956,430 A | * | 9/1990 | Tazi ............................... | 526/195 |
| 6,071,499 A | * | 6/2000 | Dupuis ........................... | 424/47 |
| 6,121,373 A | * | 9/2000 | Starch ............................ | 524/837 |
| 6,451,747 B1 | * | 9/2002 | Decoster ........................ | 510/119 |
| 7,066,966 B2 | | 6/2006 | Cottard et al. | |
| 7,204,861 B2 | | 4/2007 | Marsh et al. | |
| 7,323,015 B2 | | 1/2008 | Cottard et al. | |
| 7,410,505 B2 | | 8/2008 | Cottard et al. | |
| 2003/0147842 A1 | | 8/2003 | Restle et al. | |
| 2004/0115156 A1 | * | 6/2004 | De La Mettrie et al. ... | 424/70.15 |
| 2004/0131572 A1 | | 7/2004 | Cottard et al. | |
| 2004/0131576 A1 | | 7/2004 | Decoster et al. | |
| 2004/0133993 A1 | | 7/2004 | Cottard et al. | |
| 2004/0133994 A1 | | 7/2004 | Cottard et al. | |
| 2004/0163187 A1 | | 8/2004 | Cottard et al. | |
| 2004/0205901 A1 | | 10/2004 | Cottard et al. | |
| 2005/0169869 A1 | * | 8/2005 | Laurent et al. ............. | 424/70.13 |
| 2005/0220723 A1 | | 10/2005 | Benabdillah et al. | |
| 2005/0235431 A9 | | 10/2005 | Cottard et al. | |

FOREIGN PATENT DOCUMENTS

| | | |
|---|---|---|
| EP | 1 378 226 A1 | 1/2004 |
| EP | 1 413 288 A1 | 4/2004 |
| EP | 1 426 038 A1 | 6/2004 |
| EP | 1 600 150 A1 | 11/2005 |
| FR | 2 831 800 A1 | 5/2003 |
| FR | 2 845 908 A1 | 4/2004 |
| WO | WO 00/68282 | 11/2000 |
| WO | WO 02/058646 A1 | 8/2002 |
| WO | WO 02/058647 A1 | 8/2002 |
| WO | WO 02/058648 A1 | 8/2002 |
| WO | WO 02/096381 A1 | 12/2002 |

OTHER PUBLICATIONS

Parchem MSDA Data sheet for cetyl steary alcohol, revised Jul. 7, 2009.*
French Search Report for Application No. FR 0513195, dated Oct. 12, 2006.
English language Derwent Abstract of EP 1 600 150 A1, Nov. 30, 2005.
French Search Report for FR 0513194, dated Oct. 12, 2006.
Copending U.S. Appl. No. 11/643,864.
Office Action issued in U.S. Appl. No. 11/643,864, dated Oct. 29, 2009.
Office Action issued in U.S. Appl. No. 11/643,864, dated Oct. 28, 2010.

* cited by examiner

*Primary Examiner* — Suzanne Ziska

(74) *Attorney, Agent, or Firm* — The Marbury Law Group, PLLC

(57) ABSTRACT

Disclosed herein a cosmetic composition for treating keratin fibers, for instance, human keratin fibers such as the hair, comprising, in a cosmetically acceptable medium, at least one cationic poly(vinyllactam) polymer, at least one fatty alcohol, and at least one polyol with a molecular weight of greater than 80.

47 Claims, No Drawings

COSMETIC COMPOSITION COMPRISING AT LEAST ONE CATIONIC POLY(VINYLLACTAM), AT LEAST ONE FATTY ALCOHOL, AND AT LEAST ONE POLYOL, COSMETIC PROCESS FOR TREATING KERATIN FIBERS AND USE OF THE COMPOSITION

This application claims benefit of priority under 35 U.S.C. §119 to French Patent Application No. FR 05 13195, filed Dec. 22, 2005, the contents of which are also incorporated herein by reference.

Disclosed herein is a cosmetic composition for treating keratin fibers, for example, human keratin fibers such as the hair, comprising at least one cationic poly(vinyllactam) polymer, at least one fatty alcohol, and at least one polyol. Also disclosed herein is a haircare use of this composition and a cosmetic treatment process comprising applying the composition to keratin fibers.

The hair may be damaged and embrittled by the action of external atmospheric agents such as light and bad weather, and by mechanical or chemical treatments, such as brushing, combing, bleaching, permanent-waving, and/or dyeing. Damged hair may be difficult to manage, for example, it may be difficult to disentangle and/or style, and heads of hair, even densely populated heads of hair, may have difficulty in conserving an attractive style due to the fact that the hair lacks vigor and liveliness.

Thus, to overcome this, it is now common practice to apply to the hair haircare products comprising conditioning agents that facilitate the disentangling and combing of wet hair, thus ensuring good hold of the hairstyle and giving the hair, after drying, softness, body, volume, and/or elasticity.

These haircare products ideally have both sufficient viscosity and good spreading properties on the hair in order to be able to be, for example, in a thickened form that spreads well, such as creams and care gels that do not run onto the forehead, the nape of the neck, and/or the face, and/or into the eyes.

Moreover, this sufficient viscosity ideally makes it possible to avoid non-uniform distribution of the care product on the hair, which may lead finally to a uniform cosmetic effect on the head of hair as a whole.

These hair compositions are often formulated using fatty alcohols and generally may comprise conditioning agents chosen from cationic surfactants and silicones.

Similarly, it may be advantageous to use cationic polymers in these hair compositions to give the hair good cosmetic properties, for instance, to improve the manageability of the hair. However, the introduction of cationic polymers into these haircare compositions may give them unsatisfactory spreading properties.

Thus it would be useful to provide cosmetic compositions, for example, compositions for caring for and/or styling the hair, which do not have at least one of the drawbacks described above, while at the same time giving the hair satisfactory cosmetic properties, such as improving the manageability of the hairstyle.

The present inventors have discovered that by combining at least one cationic poly(vinyllactam) polymer, at least one fatty alcohol, and at least one polyol with a molecular weight of greater than 80, it may be possible to obtain cosmetic formulations that spread well on the hair and that have a sufficient viscosity, while at the same time giving the hair good cosmetic properties, such as improved manageability of the hair.

In at least one embodiment, the viscosity of the cosmetic composition according to the present disclosure is greater than 500 cps, measured at 25° C. at a shear rate of $1\ s^{-1}$ with a standard viscometer.

Viscometers that may be mentioned include viscometers of cone/plate geometry, for instance the Thermoelectron RS600 viscometer.

Disclosed herein is thus a cosmetic composition for treating keratin fibers, for example, human keratin fibers such as the hair, comprising at least one cationic poly(vinyllactam) polymer, at least one fatty alcohol, and at least one polyol with a molecular weight of greater than 80.

Also disclosed herein is the use of the cosmetic composition according to the present disclosure for haircare.

Further disclosed herein is a cosmetic treatment process comprising applying the cosmetic composition according to the present disclosure to keratin fibers.

Still further disclosed herein is an aerosol device comprising the composition according to the present disclosure.

Other subjects, characteristics, aspects, and advantages of the present disclosure will be understood more clearly upon reading the description and the examples that follow.

According to at least one embodiment of the present disclosure, the cosmetic composition for treating keratin fibers, for example, keratin fibers such as the hair, comprises, in a cosmetically acceptable medium:

(i) at least one cationic poly(vinyllactam) polymer comprising:
  a) at least one monomer chosen from vinyllactam and alkylvinyllactam monomers;
  b) at least one monomer chosen from those of formulas (Ia) and (Ib):

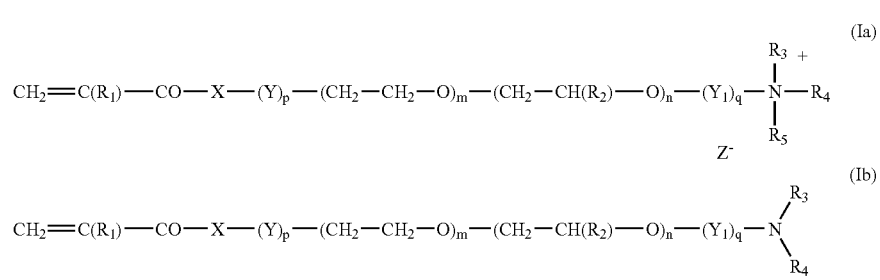

wherein:

X is chosen from oxygen and $NR_6$ radicals, $R_1$ and $R_6$, which are identical or different, are chosen from hydrogen and linear or branched $C_1$-$C_5$ alkyl radicals, $R_2$ is chosen from linear or branched $C_1$-$C_4$ alkyl radicals, $R_3$, $R_4$, and $R_5$, which are identical or different, are chosen from hydrogen, linear or branched $C_1$-$C_{30}$ alkyl radicals, and radicals of formula (II):

$$-(Y_2)_r-(CH_2-CH(R_7)-O)_x-R_8 \quad (II)$$

Y, $Y_1$, and $Y_2$, which are identical or different, are chosen from linear or branched $C_2$-$C_{16}$ alkylene radicals, $R_7$ is chosen from hydrogen, linear or branched $C_1$-$C_4$ alkyl radicals, and linear or branched $C_1$-$C_4$ hydroxyalkyl radicals, $R_8$ is chosen from hydrogen and linear or branched $C_1$-$C_{30}$ alkyl radicals, p, q, and r, which are identical or different, are equal to 0 or 1, m and n, which are identical or different, are integers ranging from 0 to 100, x is an integer ranging from 1 to 100, and Z is an organic or mineral acid anion, with the proviso that:
at least one of the substituents $R_3$, $R_4$, $R_5$, or $R_8$ is chosen from linear or branched $C_9$-$C_{30}$ alkyl radicals,
if m or n is other than zero, then q is equal to 1,
if m or n is equal to zero, then p or q is equal to 0;

(ii) at least one fatty alcohol, and (iii) at least one polyol with a molecular weight of greater than 80.

Cationic Poly(vinyllactam) Polymers

The cationic poly(vinyllactam) polymers used in the cosmetic composition according to the present disclosure may comprise:

a) at least one monomer chosen from vinyllactam and alkylvinyllactam monomers;

b) at least one monomer chosen from those of formulas (Ia) and (Ib):

$$CH_2=C(R_1)-CO-X-(Y)_p-(CH_2-CH_2-O)_m-(CH_2-CH(R_2)-O)_n-(Y_1)_q-\overset{R_{3+}}{\underset{R_5}{\overset{|}{N}}}-R_4 \quad Z^- \quad (Ia)$$

$$CH_2=C(R_1)-CO-X-(Y)_p-(CH_2-CH_2-O)_m-(CH_2-CH(R_2)-O)_n-(Y_1)_q-N\overset{R_3}{\underset{R_4}{\diagdown}} \quad (Ib)$$

wherein:

X is chosen from oxygen and $NR_6$ radicals, $R_1$ and $R_6$, which are identical or different, are chosen from hydrogen and linear or branched $C_1$-$C_5$ alkyl radicals, $R_2$ is chosen from linear or branched $C_1$-$C_4$ alkyl radicals, $R_3$, $R_4$, and $R_5$ which are identical or different, are chosen from hydrogen, linear or branched $C_1$-$C_{30}$ alkyl radicals, and radicals of formula (II):

$$-(Y_2)_r-(CH_2-CH(R_7)-O)_x-R_8 \quad (II)$$

Y, $Y_1$, and $Y_2$, which are identical or different, are chosen from linear or branched $C_2$-$C_{16}$ alkylene radicals, $R_7$ is chosen from hydrogen, linear or branched $C_1$-$C_4$ alkyl radicals, and linear or branched $C_1$-$C_4$ hydroxyalkyl radicals, $R_8$ is chosen from hydrogen and linear or branched $C_1$-$C_{30}$ alkyl radicals, p, q, and r, which are identical or different, are equal to 0 or 1, m and n, which are identical or different, are integers ranging from 0 to 100, x is chosen from 1 to 100, Z is an organic or mineral acid anion, with the proviso that:
at least one of the substituents $R_3$, $R_4$, $R_5$, or $R_8$ is chosen from linear or branched $C_9$-$C_{30}$ alkyl radicals,
if m or n is other than zero, then q is equal to 1,
if m or n is equal to zero, then p or q is equal to 0.

The cationic poly(vinyllactam) polymers used in the cosmetic composition according to the present disclosure may be crosslinked or noncrosslinked and may also be block polymers.

In at least one embodiment, the counterion $Z^-$ of the monomers of formula (Ia) may be chosen from halide ions, phosphate ions, methosulfate ions, and tosylate ions.

According to another embodiment, $R_3$, $R_4$, and $R_5$ are chosen from, independently of each other, hydrogen and linear or branched $C_1$-$C_{30}$ alkyl radicals.

In yet another embodiment, the monomer b) is chosen from monomers of formula (Ia) in which, in a further embodiment, m and n may be equal to 0.

The at least one monomer chosen from vinyllactam and alkylvinyllactam monomers may be chosen from compounds of formula (III):

$$CH(R_9)=C(R_{10})-N\overset{\diagdown}{\underset{(CH_2)_s}{\diagup}}=O \quad (III)$$

wherein:

s is an integer ranging from 3 to 6, $R_9$ is chosen from hydrogen and $C_1$-$C_5$ alkyl radicals, $R_{10}$ is chosen from hydrogen and $C_1$-$C_5$ alkyl radicals, with the proviso that at least one of the radicals $R_9$ and $R_{10}$ is hydrogen.

According to at least one embodiment, the monomer (III) is vinylpyrrolidone.

The at least one cationic poly(vinyllactam) polymer used in the composition according to the present disclosure may also comprise at least one additional monomer, chosen, for example, from cationic and nonionic monomers.

Examples of compounds suitable for use according to the present disclosure include, but are not limited to, terpolymers comprising at least:

a) one monomer of formula (III), b) one monomer of formula (Ia) wherein p=1, q=0, $R_3$ and $R_4$, which are identical or different, are chosen from hydrogen and $C_1$-$C_5$ alkyl radicals and $R_5$ is chosen from $C_9$-$C_{24}$ alkyl radicals, and c) one monomer of formula (Ib) wherein $R_3$ and $R_4$, which are identical or different, are chosen from hydrogen and $C_1$-$C_5$ alkyl radicals.

According to at least one embodiment, the terpolymers may comprise, by weight, 40% to 95% of monomer (a), 0.1% to 55% of monomer (c), and 0.25% to 50% of monomer (b). Such polymers are described, for example, in International Patent Application Publication No. WO 00/68282, which is incorporated herein by reference in its entirety.

Non-limiting examples of cationic poly(vinyllactam) polymers include vinylpyrrolidone/dimethylaminopropyl-methacrylamide/dodecyidimethylmethacryl-amidopropy-lammonium tosylate terpolymers, vinylpyrrolidone/dimethylaminopropyl-methacrylamide/cocoyldimethylmethacrylamidopropylammonium tosylate terpolymers, vinylpyrrolidone/dimethylaminopropyl-methacrylamide/lauryldimethylmethacrylami-dopropylammonium tosylate, and chloride terpolymers.

The weight-average molecular mass of the cationic poly(vinyllactam) polymers according to the present disclosure may range from 500 to 20 000 000, for instance, from 200 000 to 2 000 000, or from 400 000 to 800 000.

A non-limiting example of a suitable commercially available product is the polymer sold under the name STYLEZE W20 by the company ISP, which is a terpolymer of vinylpyrrolidone/dimethylaminopropylmethacrylamide and of lauryldimethylmethacryl-amidopropylammonium chloride.

The at least one cationic poly(vinyllactam) polymer may be present in the cosmetic composition according to the present disclosure in an amount ranging from 0.05% to 30% by weight, for example, from 0.1% to 15% by weight, or from 0.2% to 10% by weight, relative to the total weight of the composition.

Fatty Alcohols

As used herein, the term "fatty alcohol" means any saturated or unsaturated, linear or branched pure fatty alcohol comprising at least 8 carbon atoms.

The fatty alcohol is not oxyalkylenated or glycerolated.

The fatty alcohol may have the structure R—OH wherein R is chosen from saturated or unsaturated, linear or branched radicals comprising from 8 to 40, for example, from 8 to 30 carbon atoms. In at least one embodiment, R may be chosen from $C_{12}$-$C_{24}$ alkyl groups and $C_{12}$-$C_{24}$ alkenyl groups. R may optionally be substituted with at least one hydroxyl group.

Examples of fatty alcohols include, but are not limited to, lauryl alcohol, cetyl alcohol, stearyl alcohol, oleyl alcohol, behenyl alcohol, linoleyl alcohol, undecylenyl alcohol, palmitoleyl alcohol, arachidonyl alcohol and erucyl alcohol, and mixtures thereof.

The at least one fatty alcohol may represent a mixture of fatty alcohols, which means that several species of fatty alcohol may coexist, in the form of a mixture, for example, in a commercial product.

Suitable fatty alcohol mixtures include, for instance, cetyl-stearyl alcohol and cetearyl alcohol.

In at least one embodiment, the non-oxyalkylenated fatty alcohol may be solid or pasty at a temperature of 25° C. As used herein, the expression "fatty alcohol that is solid or pasty at 25° C." means a fatty alcohol that has a viscosity, measured with a rheometer at a shear rate of $1\ s^{-1}$, of greater than or equal to 1 Pa·s.

According to another embodiment, the fatty alcohols used in the cosmetic composition according to the present disclosure are chosen from cetyl alcohol and cetearyl alcohol.

The at least one fatty alcohol may be present in the composition in an amount ranging from 0.1% to 30%, for example, from 0.2% to 20%, or from 0.5% to 10% by weight, relative to the total weight of the composition.

Polyols

The at least one polyol used in the cosmetic composition according to the present disclosure has a molecular weight of greater than 80.

In at least one embodiment, the polyols that may be used in the cosmetic composition according to the disclosure are polyols with a molecular weight ranging from 90 to 350 and chosen from those of formula (V):

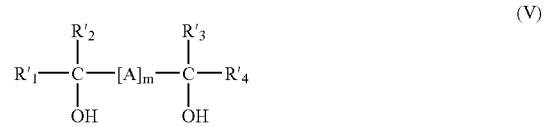

wherein:

$R'_1$, $R'_2$, $R'_3$, and $R'_4$, which are identical or different, are chosen from hydrogen, $C_1$-$C_6$ alkyl radicals, and $C_1$-$C_6$ mono- or polyhydroxyalkyl radicals, A is chosen from linear or branched alkylene radicals comprising from 1 to 18 carbon atoms and from 0 to 9 oxygen atoms, and m is equal to 0 or 1.

According to one embodiment, the at least one polyol may be chosen from polyols of formula (V), wherein m=0, such as 1,2,3-propanetriol, pinacol(2,3-dimethyl-2,3-butanediol), 1,2,3-butanetriol, 2,3-butanediol, and sorbitol.

According to another embodiment, the at least one polyol may be chosen from polyols of formula (V), wherein m=1 and $R'_1$, $R'_2$, $R'_3$, and $R'_4$ which are identical or different, are chosen from hydrogen and $C_1$-$C_6$ alkyl radicals. A non-limiting example of such polyols is polyethylene glycols, such as the product known as PEG-6 in the CTFA publication (International Cosmetic Ingredient Dictionary, 7th edition).

In yet another embodiment, the at least one polyol is chosen from polyols of formula (V), wherein m=1 and $R'_1$, $R'_2$, $R'_3$, and $R'_4$, which are identical or different, are chosen from hydrogen and $C_1$-$C_6$ alkyl radicals, and whose molecular weight is less than 200. Such polyols may be chosen from, for example, 3-methyl-1,3,5-pentanetriol, 1,2,4-butanetriol, 1,5-pentanediol, 2-methyl-1,3-propanediol, 1,3-butanediol, 3-methyl-1,5-pentanediol, neopentyl glycol(2,2-dimethyl-1,3-propanediol), isoprene glycol(3-methyl-1,3-butanediol), and hexylene glycol(2-methyl-2,4-pentanediol). In a further embodiment, these polyols may be chosen from hexylene glycol, neopentyl glycol, and 3-methyl-1,5-pentanediol.

According to still a further embodiment, the polyol used in the cosmetic composition according to the present disclosure is 1,2,3-propanetriol.

The at least one polyol may be present in the composition in an amount ranging from 0.1% to 30% by weight, for example, from 0.5% to 20% by weight, or from 1% to 15% by weight, relative to the total weight of the cosmetic composition.

In at least one embodiment, the cationic polyvinyllactam/fatty alcohol weight ratio may range from 0.1 to 5, the cationic polyvinyllactam/polyol weight ratio may range from 0.01 to 5, and the fatty alcohol/polyol weight ratio may range from 0.01 to 5.

Silicones

The cosmetic composition according to the present disclosure may also comprise at least one silicone.

As used herein, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and comprising a repetition of main units in which the silicon atoms are linked together via oxygen atoms (siloxane bond —Si—O—Si—), optionally substituted hydrocarbon-based radicals being directly linked via a carbon atom to the said silicon atoms. The hydrocarbon-based radicals may be chosen, for example, from alkyl radicals, such as $C_1$-$C_{10}$ radicals, for instance, methyl; fluoroalkyl radicals, the alkyl part of which is $C_1$-$C_{10}$; and aryl radicals such as phenyl.

In at least one embodiment, the silicone is an oxyalkylenated silicone.

As used herein, the term "oxyalkylenated silicone" means any silicone comprising at least one oxyalkylene group of the type (—$C_xH_{2x}O$—)$_a$ in which x may range from 2 to 6 and a is greater than or equal to 2.

The oxyalkylenated silicones that may be used in the cosmetic composition may be chosen, for example, from silicones of formulas (VI), (VII), (VIII), (IX), and (X) below:

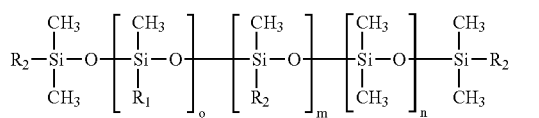

(VI)

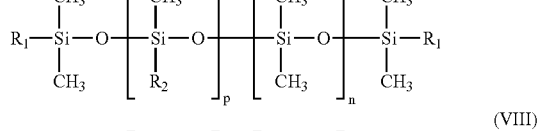

(VII)

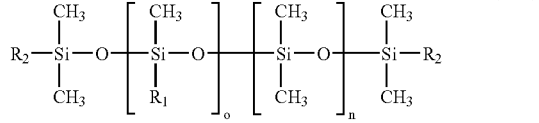

(VIII)

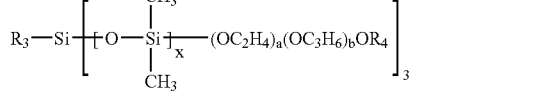

(IX)

wherein:

$R_1$, which may be identical or different, is chosen from linear or branched $C_1$-$C_{30}$ alkyl radicals and phenyl radicals, $R_2$, which may be identical or different, is chosen from —$C_cH_{2c}$—O—($C_2H_4O$)$_a$($C_3H_6O$)$_b$—$R_5$ and —$C_cH_{2c}$—O—($C_4H_8O$)$_a$—$R_5$ radicals, $R_3$ and $R_4$, which may be identical or different, are chosen from linear or branched $C_1$ to $C_{12}$ alkyl radicals, for instance, methyl radicals, $R_5$, which may be identical or different, is chosen from hydrogen, linear or branched alkyl radicals comprising from 1 to 12 carbon atoms, linear or branched alkoxy radicals comprising from 1 to 6 carbon atoms, linear or branched acyl radicals comprising from 2 to 30 carbon atoms, hydroxyl radicals, —$SO_3M$ radicals, $C_1$-$C_6$ aminoalkoxy radicals optionally substituted on the amine, $C_2$-$C_6$ aminoacyl radicals optionally substituted on the amine, —NHCH$_2$CH$_2$COOM radicals, —N(CH$_2$CH$_2$COOM)$_2$ radicals, aminoalkyl radicals optionally substituted on the amine and/or on the alkyl chain, $C_2$-$C_{30}$ carboxyacyl radicals, groups optionally substituted with one or two substituted aminoalkyl radicals, —CO(CH$_2$)$_d$COOM groups, —COCHR$_7$(CH$_2$)$_d$COOM groups, —NHCO(CH$_2$)$_d$OH groups, —NH$_3$Y groups, and phosphate groups, M, which may be identical or different, is chosen from hydrogen, Na, K, Li, NH$_4$, and organic amines, $R_7$ is chosen from hydrogen atom and —SO$_3$M radicals, d is a number ranging from 1 to 10, m is a number ranging from 0 to 20, n is a number ranging from 0 to 500, o is a number ranging from 0 to 20, p is a number ranging from 1 to 50, a is a number ranging from 0 to 50, b is a number ranging from 0 to 50, a+b is greater than or equal to 2, c is a number ranging from 0 to 4, x is a number ranging from 1 to 100, Y is chosen from monovalent mineral or organic anions such as halides (e.g., chloride and bromide), sulfates, and carboxylates (e.g., acetate, lactate, and citrate), with the proviso that when the silicone is chosen from silicones of formula (VII) wherein $R_5$ is hydrogen, then n is greater than 12.

Such silicones are sold, for example, by the company Goldschmidt under the trade names ABIL WE 09, ABIL EM 90, ABIL B8852, ABIL B8851, ABIL B8843, and ABIL B8842, by the company Dow Corning under the names FLUID DC 190, DC3225 C, Q2-5220, Q25354, and Q2-5200, by the company Rhodia Chimie under the names SILBIONE OIL 70646 and RHODORSIL OIL 10634, by the company General Electric under the names SF1066 and SF1188, by the company SWS Silicones under the name SILICONE COPOLYMER F 754, by the company Amerchol under the name SILSOFT BEAUTY AID SL, by the company Shin-Etsu under the name KF 351, by the company Wacker under the name BELSIL DMC 6038, by the company Siltech under the names SILWAX WD-C, SILWAX WD-B, SILWAX WD-IS, SILWAX WSL, SILWAX DCA 100 and SILTECH AMINE 65, by the company Fanning Corporation under the names FANCORSIL SLA and FANCORSIL LIM1, and by the company Phoenix under the name PECOSIL.

These silicones are described, for example, in U.S. Pat. Nos. 5,070,171, 5,149,765, 5,093,452, and 5,091,493.

In at least one embodiment, polyoxyalkylenated silicones chosen from those of formulas (VII) and (VIII) may be used. According to another embodiment, these formulas satisfy at least one of the following conditions:

c is equal to 2 or 3, $R_1$ is a methyl radical, $R_5$ is chosen from methyl radicals, $C_{12}$-$C_{22}$ acyl radicals, and CO(CH$_2$)$_d$COOM, a is a number ranging from 2 to 25, for example, from 2 to 15, b is equal to 0, n is a number ranging from 0 to 100, and p is a number ranging from 1 to 20.

The polyoxyalkylenated silicones according to the present disclosure may also be chosen from the silicones of formula (X):

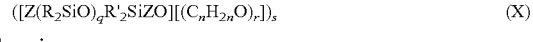

(X)

wherein:

$R_2$ and $R'_2$, which may be identical or different, are chosen from monovalent $C_1$-$C_{30}$ hydrocarbon-based radicals, n is an integer ranging from 2 to 4, q is a number greater than or equal to 4, for example, ranging from 4 to 200, or from 4 to 100, r is a number greater than or equal to 4, for example, ranging from 4 to 200, or from 5 to 100, s is a number greater than or equal to 4, for example, ranging from 4 to 1000, or from 5 to 300, Z is chosen from divalent organic groups linked to the adjacent silicon atom via a carbon-silicon bond and to the polyoxyalkylene block ($C_nH_{2n}O$) via an oxygen atom, the average molecular weight of each siloxane block ranges from 400 to 10 000, and the average molecular weight of each polyoxyalkylene block ranges from 300 to 10 000, the siloxane blocks are present in the block copolymer in an amount ranging from about 10% to about 95% by weight of the block copolymer, and the number-average molecular weight of the block copolymer ranges from 2500 to 1 000 000, for example, from 3000 to 200 000, or from 6000 to 100 000.

$R_2$ and $R'_2$ may be chosen from linear or branched alkyl radicals, for instance, methyl, ethyl, propyl, butyl, pentyl, hexyl, octyl, decyl, and dodecyl radicals, aryl radicals, for instance, phenyl and naphthyl, aralkyl, and alkylaryl radicals, for instance, benzyl and phenylethyl, and tolyl and xylyl radicals.

Z may be chosen, for example, from —R"—, —R"—CO—, —R"—NHCO—, —R"—NH—CO—NH—R"'— and —R"—OCONH—R"'—NHCO—, wherein R" is chosen from linear or branched $C_1$-$C_6$ divalent alkylene groups, for instance, ethylene, propylene, and linear or branched butylene, and R"' is chosen from divalent alkylene groups and divalent arylene groups, for instance —$C_6H_4$—, —$C_6H_4$—$C_6H_4$—, —$C_6H_4$—$CH_2$—$C_6H_4$—, and —$C_6H_4$—$C(CH_3$—$C_6H_4$—.

According to at least one embodiment, Z may be chosen from divalent alkylene radicals, such as linear or branched —$C_3H_6$— radicals and —$C_4H_8$— radicals.

The preparation of the block copolymers used in the context of the present disclosure is described, for instance, in European Patent Application No. EP 0 492 657 A1, which is incorporated herein by reference in its entirety.

Such products are sold, for example, under the name SILICONE FLUID FZ-2172 by the company OSI.

The silicones that may be used in the compositions according to the present disclosure may be in the form of aqueous solutions or optionally in a form chosen from aqueous dispersions and emulsions.

The at least one silicone that may be used in the cosmetic composition may also be chosen from silicone gums.

The silicone gums that may be used in the cosmetic composition include, but are not limited to, polydiorganosiloxanes having high number-average molecular masses ranging from 200 000 to 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, tridecane, and mixtures thereof.

Non-limiting examples of silicone gums include:
polydimethylsiloxane
polydimethylsiloxane/methylvinylsiloxane gums,
polydimethylsiloxane/diphenylsiloxane,
polydimethylsiloxane/phenylmethylsiloxane, and
polydimethylsiloxane/diphenylsiloxane/methylvinylsiloxane.

Examples of mixtures of such compounds include, but are not limited to:
mixtures formed from a polydimethylsiloxane hydroxylated at the end of the chain, or dimethiconol (CTFA) and from a cyclic polydimethylsiloxane also called cyclomethicone (CTFA), such as the product Q2 1401 sold by the company Dow Corning;

mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500 000, dissolved in the oil SF 1202 SILICONE FLUID corresponding to decamethylcyclopentasiloxane;

mixtures of two PDMSs of different viscosities, for example, of a PDMS gum and a PDMS oil, such as the product SF 1236 from the company General Electric. The product SF 1236 is a mixture of an SE 30 gum defined above, having a viscosity of 20 $m^2$/s, and an SF 96 oil, with a viscosity of $5\times10^{-6}$ $m^2$/s. This product may contain 15% SE 30 gum and 85% SF 96 oil.

The at least one silicone that may be used in the cosmetic composition may also be chosen from amino silicones.

As used herein, the term "amino silicone" means any silicone comprising at least one function chosen from primary, secondary, and tertiary amine functions and/or a quaternary ammonium group.

The amino silicones that may be used in the cosmetic composition may be chosen, for example, from:

(a) compounds of formula (XI) below:

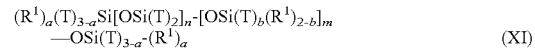

$(R^1)_a(T)_{3-a}Si[OSi(T)_2]_n$-$[OSi(T)_b(R^1)_{2-b}]_m$
—$OSi(T)_{3-a}$-$(R^1)_a$  (XI)

wherein:

T is chosen from hydrogen, phenyl radicals, hydroxyl (—OH) radicals, and $C_1$-$C_8$ alkyl radicals, for instance, methyl radicals, and $C_1$-$C_8$ alkoxy radicals, such as methoxy radicals, a is an integer ranging from 0 to 3, and, in at least one embodiment, is equal to 0, b is equal to 0 or 1, and in at least one embodiment, is equal to 1, m and n are numbers such that the sum (n+m) can range from 1 to 2000, for instance, from 50 to 150, wherein n is a number ranging from 0 to 1999, for example, from 49 to 149, and m is a number ranging from 1 to 2000, for example, from 1 to 10;

$R^1$ is a monovalent radical of formula —$C_qH_{2q}L$ wherein q is a number ranging from 2 to 8 and L is an optionally quaternized amino group chosen from:

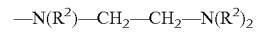
—N($R^2$)—$CH_2$—$CH_2$—N($R^2$)$_2$

—N($R^2$)$_2$

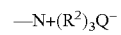
—N+($R^2$)$_3$Q$^-$

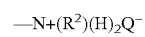
—N+($R^2$)(H)$_2$Q$^-$

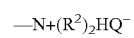
—N+($R^2$)$_2$HQ$^-$

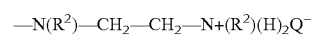
—N($R^2$)—$CH_2$—$CH_2$—N+($R^2$)(H)$_2$Q$^-$ wherein $R^2$ is chosen from hydrogen, phenyl radicals, benzyl radicals, and saturated monovalent hydrocarbon-based radicals, for example, $C_1$-$C_{20}$ alkyl radicals, and Q$^-$ is a halide ion, for example, fluoride, chloride, bromide, and iodide.

In at least one embodiment, the amino silicones of formula (XI) may be chosen from the compounds of formula (XII):

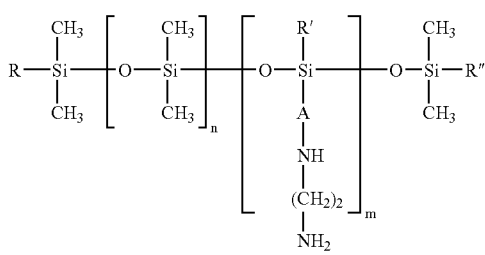

(XII)

wherein R, R', and R", which may be identical or different, are chosen from $C_1$-$C_4$ alkyl radicals, such as $CH_3$ radicals; $C_1$-$C_4$ alkoxy radicals, such as methoxy radicals; and OH; A is chosen from linear or branched, $C_3$-$C_8$, for instance, $C_3$-$C_6$ alkylene radicals; m and n are integers dependent on the molecular weight and whose sum ranges from 1 to 2000.

According to one embodiment, R, R', and R", which may be identical or different, are chosen from $C_1$-$C_4$ alkyl radicals and hydroxyl radicals, A is a $C_3$ alkylene radical, and m and n are such that the weight-average molecular mass of the compound ranges from 5000 to 500 000. Compounds of this type are referred to in the CTFA dictionary as "amodimethicones".

According to another embodiment, R, R', and R", which may be identical or different, are chosen from $C_1$-$C_4$ alkoxy radicals and hydroxyl radicals, at least one of the radicals R or R" is an alkoxy radical, and A is a $C_3$ alkylene radical. The hydroxyl/alkoxy molar ratio may range from 0.2/1 to 0.4/1, and in at least one embodiment, may be equal to 0.3/1. Moreover, m and n may be such that the weight-average molecular mass of the compound ranges from 2000 to $10^6$. In one embodiment, n may range from 0 to 999 and m may range from 1 to 1000, such that the sum of n and m ranges from 1 to 1000.

In this category of compounds, mention may be made, inter alia, of the product Belsil® ADM 652 sold by Wacker.

According to a further embodiment, R and R", which are different, are chosen from $C_1$-$C_4$ alkoxy radicals and hydroxyl radicals, at least one of the radicals R or R" is an alkoxy radical, R' is a methyl radical, and A is a $C_3$ alkylene radical. The hydroxyl/alkoxy molar ratio may range from 1/0.8 to 1/1.1, and in at least one embodiment, is equal to 1/0.95. Moreover, m and n may be such that the weight-average molecular mass of the compound ranges from 2000 to 200 000. According to one embodiment, n may range from 0 to 999 and m may range from 1 to 1000, such that the sum of n and m ranges from 1 to 1000.

A non-limiting example of a commercial product corresponding to this embodiment is the product Fluid WR® 1300 sold by the company Wacker.

According to yet another embodiment, R and R" are hydroxyl radicals, R' is a methyl radical, and A is a $C_4$-$C_8$, for instance, a $C_4$ alkylene radical. Moreover, m and n may be such that the weight-average molecular mass of the compound ranges from 2000 to $10^6$. In at least one embodiment, n may range from 0 to 1999 and m may range from 1 to 2000, such that the sum of n and m ranges from 1 to 2000.

An exemplary commercial product corresponding to this embodiment is sold under the name DC 28299 by Dow Corning.

According to the present disclosure the molecular mass of these silicones is determined by gel permeation chromatography (ambient temperature, polystyrene standard; µ styragem columns; eluent THF; flow rate 1 mm/m; 200 µl of a solution containing 0.5% by weight of silicone are injected into THF and detection is performed by UV refractometry).

A non-limiting product corresponding to the definition of formula (XI) is the polymer known in the CTFA dictionary as "trimethylsilyl amodimethicone", corresponding to formula (XIII):

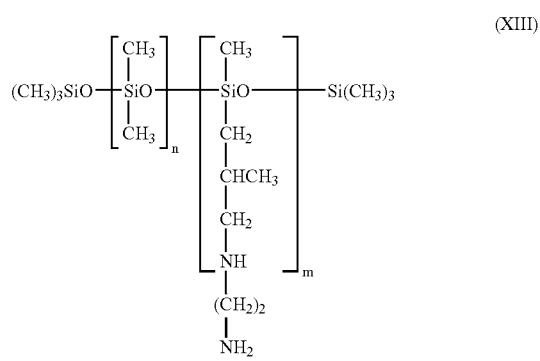

(XIII)

wherein n and m have the meanings given above in accordance with formula (XI).

Such compounds are described, for example, in European Patent Application No. 0 095 238; and a compound of formula (XIII) is sold, for example, under the name Q2-8220 by the company OSI.

(b) compounds corresponding to formula (XIV):

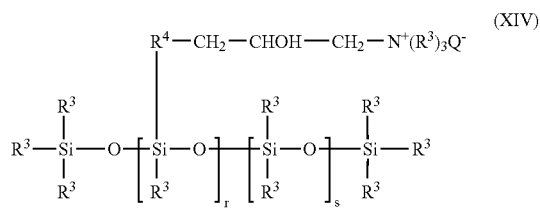

(XIV)

wherein:

$R^3$ is chosen from monovalent $C_1$-$C_{18}$ hydrocarbon-based radicals, such as $C_1$-$C_{18}$ alkyl radicals and $C_2$-$C_{18}$ alkenyl radicals, for example methyl radicals, $R^4$ is chosen from divalent hydrocarbon-based radicals, such as $C_1$-$C_{18}$ alkylene radicals and $C_1$-$C_{18}$, for example, $C_1$-$C_8$, alkylenoxy radicals;

$Q^-$ is a halide ion, such as chloride;

r is an average statistical value ranging from 2 to 20, for example, from 2 to 8; and s is an average statistical value ranging from 20 to 200, for example, from 20 to 50.

Such compounds are described, for example, in U.S. Pat. No. 4,185,087. A non-limiting example of a compound falling within this embodiment is the product sold by the company Union Carbide under the name UCAR SILICONE ALE 56.

(c) quaternary ammonium silicones of formula (XV):

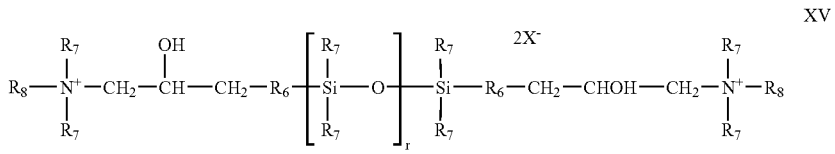

wherein:

$R_7$, which may be identical or different, is chosen from monovalent hydrocarbon-based radicals comprising from 1 to 18 carbon atoms, such as $C_1$-$C_{18}$ alkyl radicals, $C_2$-$C_{18}$ alkenyl radicals and rings comprising 5 or 6 carbon atoms, for example, methyl radicals;

$R_6$ is chosen from divalent hydrocarbon-based radicals, such as $C_1$-$C_{18}$ alkylene radicals and divalent $C_1$-$C_{18}$, for example $C_1$-$C_8$, alkyleneoxy radicals linked to the Si via an SiC bond;

$R_8$, which may be identical or different, is chosen from hydrogen, monovalent hydrocarbon-based radicals comprising from 1 to 18 carbon atoms, for example, $C_1$-$C_{18}$ alkyl radicals, $C_2$-$C_{18}$ alkenyl radicals, and —$R_6$—NHCOR$_7$ radicals;

$X^-$ is an anion chosen from halide ions, for example, chloride, and organic acid salts (acetate, etc.); and r is a mean statistical value ranging from 2 to 200, for example, from 5 to 100.

These silicones are described, for example, in European Patent Application No. 0 530 974.

(d) amino silicones of formula (XVI):

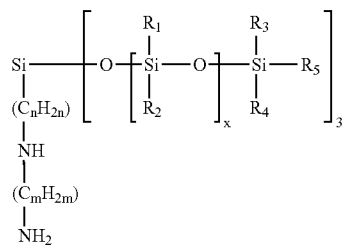

wherein:

$R_1$, $R_2$, $R_3$, and $R_4$, which may be identical or different, are chosen from $C_1$-$C_4$ alkyl radicals and phenyl groups, $R_5$ is chosen from $C_1$-$C_4$ alkyl radicals and hydroxyl groups, n is an integer ranging from 1 to 5, m is an integer ranging from 1 to 5, and x is chosen such that the amine number ranges from 0.01 to 1 meq/g.

According to one embodiment, the at least one silicone may be chosen from polysiloxanes containing at least one amine group such as amodimethicones and trimethylsilylamodimethicones (CTFA, 4th edition, 1997), and in another embodiment, the at least one silicone may be chosen from silicones containing at least one quaternary ammonium group.

When at least one silicone compound is present in the composition according to the present disclosure, in at least one embodiment, it may be combined with at least one surfactant chosen from cationic and nonionic surfactants.

For example, the product sold under the name CATIONIC EMULSION DC 929 by the company Dow Corning may be used, which comprises, besides amodimethicone, a cationic surfactant comprising a mixture of products corresponding to the formula:

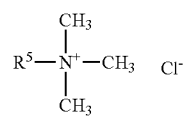

wherein $R^5$ is chosen from $C_{14}$-$C_{22}$ alkenyl and/or alkyl radicals derived from tallow fatty acids, and known under the CTFA name tallowtrimonium chloride, in combination with a nonionic surfactant of formula:

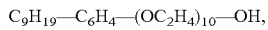

known under the CTFA name as Nonoxynol 10.

Further, the product sold under the name CATIONIC EMULSION DC 939 by the company Dow Corning may be used, which comprises, besides amodimethicone, a cationic surfactant which is trimethylcetylammonium chloride and a nonionic surfactant of formula: $C_{13}H_{27}$—$(OC_2H_4)_{12}$—OH, known under the CTFA name trideceth-12.

Another commercial product that may be used according to the present disclosure is the product sold under the name Dow Corning Q2 7224 by the company Dow Corning, comprising, in combination, the trimethylsilyl amodimethicone of formula (C) described above, a nonionic surfactant of formula: $C_8H_{17}$—$C_6H_4$—$(OCH_2CH_2)_{40}$—OH, known under the CTFA name octoxynol-40, a second nonionic surfactant of formula: $C_{12}H_{25}$—$(OCH_2$—$CH_2)_6$—OH, known under the CTFA name isolaureth-6, and propylene glycol.

Fixing Polymers

The cosmetic composition may also comprise at least one additional fixing polymer other than the polymers of the present disclosure.

As used herein, the term "fixing polymer" means any polymer that makes it possible to impart a given shape and/or to maintain a given shape or hairstyle.

The fixing polymers that may be used in the cosmetic composition according to the present disclosure may be chosen from cationic, anionic, amphoteric, and nonionic polymers, and mixtures thereof.

As used herein, the term "cationic polymer" means any polymer comprising at least one group chosen from cationic groups and/or groups that may be ionized into cationic groups.

Cationic Fixing Polymers

The cationic fixing polymers that may be used according to the present disclosure may be chosen, for example, from polymers comprising at least one group chosen from primary, secondary, tertiary, and/or quaternary amine groups forming part of the polymer chain or directly attached thereto, and having a number average molecular weight ranging from 500 to 5 000 000, for example, from 1000 to 3 000 000.

Examples of such polymers include, but are not limited to:

(1) homopolymers and copolymers derived from acrylic or methacrylic esters or amides with amine functions, and comprising at least one unit chosen from those of formulas (A)-(C):

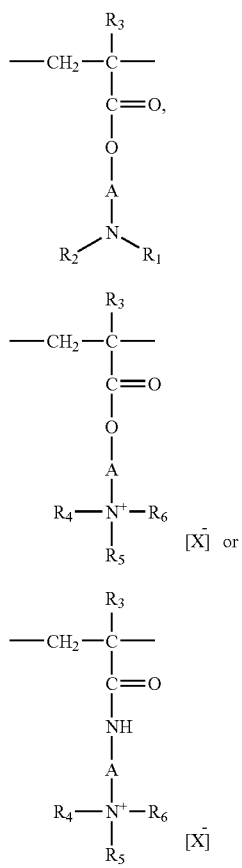

wherein:

$R_1$ and $R_2$, which may be identical or different, are chosen from hydrogen and alkyl groups comprising from 1 to 6 carbon atoms;

$R_3$ is chosen from hydrogen and $CH_3$;

A is chosen from linear or branched alkyl groups comprising from 1 to 6 carbon atoms and hydroxyalkyl groups comprising from 1 to 4 carbon atoms;

$R_4$, $R_5$, and $R_6$, which may be identical or different, are chosen from alkyl groups comprising from 1 to 18 carbon atoms and benzyl groups; and X is chosen from methosulfate anions and halides such as chloride and bromide.

The copolymers of the family (1) may also comprise at least one comonomer unit that may be chosen from acrylamides, methacrylamides, diacetone acrylamides, acrylamides and methacrylamides substituted on the nitrogen with lower ($C_{1-4}$) alkyl groups, groups derived from acrylic or methacrylic acids or esters thereof, vinyllactams such as vinylpyrrolidone and vinylcaprolactam, and vinyl esters.

Thus, non-limiting examples of copolymers of the family (1) include:

copolymers of acrylamide and of dimethylaminoethyl methacrylate quaternized with dimethyl sulfate or with a dimethyl halide, such as the product sold under the name Hercofloc® by the company Hercules, copolymers of acrylamide and of methacryloyloxyethyltrimethylammonium chloride, described, for example, in European Patent Application No. 0 080 976 and sold under the name BINA QUAT P 100 by the company Ciba Geigy, copolymers of acrylamide and of methacryloyloxyethyltrimethylammonium methosulfate, such as the product sold under the name RETEN by the company Hercules, quaternized or non-quaternized vinylpyrrolidone/dialkylaminoalkyl acrylate or methacrylate copolymers, such as the products sold under the name Gafquat® by the company ISP, such as, for example, Gafquat® 734 and Gafquat® 755, and the products known as Copolymer® 845, 958, and 937. These polymers are described, for example, in French Patent Nos. 2 077 143 and 2 393 573, dimethylaminoethyl methacrylate/vinylcaprolactam/vinylpyrrolidone terpolymers, such as the product sold under the name Gaffix® VC 713 by the company ISP, and quaternized vinylpyrrolidone/dimethylaminopropylmethacrylamide copolymers, such as the product sold under the name Gafquat® HS 100 by the company ISP;

(2) cationic polysaccharides, optionally comprising quaternary ammonium, such as those described in U.S. Pat. Nos. 3,589,578 and 4,031,307, such as guar gums comprising trialkylammonium cationic groups. Such products are sold, for example, under the trade names JAGUAR C13S, JAGUAR C15, and JAGUAR C17 by the company Meyhall;

(3) quaternary copolymers of vinylpyrrolidone and of vinylimidazole;

(4) chitosans and salts thereof; such as chitosan acetate, lactate, glutamate, gluconate, and pyrrolidonecarboxylate.

Examples of these compounds include, for instance, chitosan having a degree of deacetylation of 90.5% by weight, sold under the name KYTAN BRUT STANDARD by the company Aber Technologies, and chitosan pyrrolidonecarboxylate sold under the name Kytamer® PC by the company Amerchol.

(5) cationic cellulose derivatives such as copolymers of cellulose or of cellulose derivatives grafted with a water-soluble monomer comprising a quaternary ammonium, and disclosed, for instance, in U.S. Pat. No. 4,131,576, such as hydroxyalkylcelluloses, for instance hydroxymethyl-, hydroxyethyl-, and hydroxy-propylcelluloses grafted, for example, with a methacryloyloxyethyltrimethylammonium, methacrylamidopropyltrimethylammonium or dimethyldiallylammonium salt.

Commercial products sold corresponding to this definition include, for example, the products sold under the name CELQUAT L 200 and CELQUAT H 100 by the company National Starch.

Anionic Fixing Polymers

The anionic fixing polymers which may be used may be chosen from polymers comprising groups derived from an acid chosen from carboxylic acid, sulfonic acid, and phosphoric acid and have a number average molecular weight ranging from 500 to 5 000 000.

The carboxylic groups may be provided by unsaturated monocarboxylic or dicarboxylic acid monomers such as those corresponding to the formula:

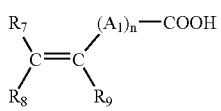

wherein n is an integer ranging from 0 to 10, $A_1$ is a methylene group, optionally connected to the carbon atom of the unsaturated group, or to the neighboring methylene group when n is greater than 1, via a hetero atom such as oxygen and sulfur, $R_7$ is chosen from hydrogen, phenyl groups, and benzyl groups, $R_8$ is chosen from hydrogen, lower alkyl groups, and carboxyl groups, $R_9$ is chosen from hydrogen, lower alkyl groups, —$CH_2$—COOH, phenyl groups, and benzyl groups.

In the abovementioned formula, a lower alkyl group may denote a group comprising from 1 to 4 carbon atoms, such as methyl and ethyl groups.

The anionic fixing polymers may be chosen, for example, from:

A) acrylic or methacrylic acid homo- or copolymers, and salts thereof, such as the products sold under the names Versicol® E and K by the company Allied Colloid and Ultrahold® by the company BASF, the copolymers of acrylic acid and of acrylamide sold in the form of their sodium salts under the names RETEN 421, 423, and 425 by the company Hercules, and the sodium salts of polyhydroxycarboxylic acids.

B) copolymers of acrylic or methacrylic acid with a monoethylenic monomer such as ethylene, styrene, vinyl esters, acrylic acid esters, and methacrylic acid esters, optionally grafted onto a polyalkylene glycol such as polyethylene glycol and optionally crosslinked. Such polymers are described, for example, in French Patent No. 1 222 944 and German Patent Application No. 2 330 956, the copolymers of this type comprising an optionally N-alkylated and/or hydroxyalkylated acrylamide unit in their chain as described, for instance, in Luxembourg Patent Application Nos. 75370 and 75371 or sold under the name QUADRAMER by the company American Cyanamid. Methacrylic acid/ethyl acrylate/tert-butyl acrylate terpolymers such as the product sold under the name Luvimer® 100 P by the company BASF and ethacrylic acid/acrylic acid/ethyl acrylate/methyl methacrylate copolymers as an aqueous dispersion, sold under the name Amerhold® DR 25 by the company Amerchol may also be used.

C) crotonic acid copolymers, such as those comprising vinyl acetate or propionate units in their chain and optionally other monomers such as allylic esters, methallylic esters, vinyl ethers, and vinyl esters of a linear or branched saturated carboxylic acid with a long hydrocarbon chain such as those comprising at least 5 carbon atoms, it being possible for these polymers optionally to be grafted or crosslinked, or alternatively another monomer chosen from vinyl, allylic, and methallylic ester monomers of an α- or β-cyclic carboxylic acid. Such polymers are described, for example, in French Patent Nos. 1 222 944, 1 580 545, 2 265 782, 2 265 781, 1 564 110, and 2 439 798. Commercial products falling into this class include, for instance, the resins 28-29-30, 26-13-14, and 28-13-10 sold by the company National Starch.

D) copolymers derived from $C_4$-$C_8$ monounsaturated carboxylic acids or anhydrides chosen from:

copolymers comprising (i) at least one entity chosen from maleic, fumaric, and itaconic acids and anhydrides and (ii) at least one monomer chosen from vinyl esters, vinyl ethers, vinyl halides, phenylvinyl derivatives, acrylic acid and its esters, the anhydride functions of these copolymers optionally being monoesterified or monoamidated. Such polymers are described, for example, in U.S. Pat. Nos. 2,047,398, and 2,723,248, French Patent No. 2,102,113 and British Patent No. 839 805, and are sold, for instance, under the names Gantrez® AN and ES by the company ISP, copolymers comprising (i) at least one unit chosen from maleic, citraconic, and itaconic anhydride units and (ii) at least one monomer chosen from allylic and methallylic esters optionally comprising at least one group chosen from acrylamide, methacrylamide, α-olefin, acrylic or methacrylic ester, acrylic or methacrylic acid, and vinylpyrrolidone groups in their chain, the anhydride functions of these copolymers optionally being monoesterified or monoamidated.

These polymers are described, for example, in French Patent Nos. 2 350 384 and 2 357 241.

E) polyacrylamides comprising carboxylate groups.

The homopolymers and copolymers comprising sulfonic groups may be chosen from polymers comprising at least one unit chosen from vinylsulfonic, styrenesulfonic, naphthalenesulfonic, and acrylamidoalkylsulfonic units.

These polymers may be chosen, for example, from:

polyvinylsulfonic acid salts having a molecular weight ranging from 1000 to 100 000, as well as the copolymers with an unsaturated comonomer such as acrylic and methacrylic acids and their esters, as well as acrylamide and its derivatives, vinyl ethers, and vinylpyrrolidone;

polystyrenesulfonic acid salts such as the sodium salts that are sold under the names Flexan® 500 and Flexan® 130 by National Starch. These compounds are also described, for example, in French Patent No. 2 198 719;

polyacrylamidesulfonic acid salts, such as those described in U.S. Pat. No. 4,128,631, such as the polyacrylamidoethylpropanesulfonic acid sold under the name COSMEDIA POLYMER HSP 1180 by Henkel.

According to at least one embodiment, the anionic fixing polymers may be chosen from acrylic acid copolymers, such as the acrylic acid/ethyl acrylate/N-tert-butylacrylamide terpolymers sold under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold under the name RESIN 28-29-30 by the company National Starch, polymers derived from maleic, fumaric, or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by the company ISP, the copolymers of methacrylic acid and of methyl methacrylate sold under the name Eudragit® L by the company Rohm Pharma, the copolymers of methacrylic acid and of ethyl acrylate sold under the name Luvimer® MAEX or MAE by the company BASF, the vinyl acetate/crotonic acid copolymers sold under the name LUVISET CA 66 by the company BASF, and the vinyl acetate/crotonic acid copolymers grafted with polyethylene glycol sold under the name Aristoflex® by the company BASF.

According to another embodiment the anionic fixing polymers may be chosen from methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name RESIN 28-29-30 by the company National Starch, and the copolymers of methacrylic acid and of ethyl acrylate sold under the name Luvimer® MAEX or MAE by the company BASF.

Amphoteric Fixing Polymers

The amphoteric fixing polymers that can be used in accordance with the present disclosure may be chosen from polymers comprising units B and C distributed randomly in the polymer chain, wherein B is a unit derived from a monomer comprising at least one basic nitrogen atom and C is a unit derived from an acid monomer comprising at least one group chosen from carboxylic and sulfonic groups, or alternatively, B and C may be chosen from groups derived from carboxybetaine or sulfobetaine zwitterionic monomers;

B and C may also be chosen from cationic polymer chains comprising primary, secondary, tertiary or quaternary amine groups, in which at least one of the amine groups bears a group chosen from carboxylic and sulfonic groups connected via a hydrocarbon group, or alternatively, B and C may form part of a chain of a polymer containing an α,β-dicarboxylic ethylene unit in which one of the carboxylic groups has been made to react with a polyamine comprising at least one group chosen from primary and secondary amine groups.

Non-limiting examples of amphoteric fixing polymers corresponding to the definition given above include:

(1) copolymers comprising acidic vinyl and basic vinyl units, such as those resulting from the copolymerization of a monomer derived from a vinyl compound bearing a carboxylic group such as, acrylic acid, methacrylic acid, maleic acid, α-chloroacrylic acid, and a basic monomer derived from a substituted vinyl compound containing at least one basic atom, such as dialkylaminoalkyl methacrylate and acrylate, dialkylaminoalkylmethacrylamides and -acrylamides. Such compounds are described, for example, in U.S. Pat. No. 3,836,537.

(2) polymers comprising units derived from:
a) at least one monomer chosen from acrylamides and methacrylamides substituted on the nitrogen atom with an alkyl group,
b) at least one acidic comonomer comprising at least one reactive carboxylic group, and
c) at least one basic comonomer such as esters containing primary, secondary, tertiary, and quaternary amine substituents of acrylic and methacrylic acids and the product of quaternization of dimethylaminoethyl methacrylate with dimethyl or diethyl sulfate.

N-substituted acrylamides and methacrylamides may be chosen from compounds in which the alkyl groups comprises from 2 to 12 carbon atoms, such as N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers may be chosen, for example, from acrylic acid, methacrylic acid, crotonic acid, itaconic acid, maleic acid, and fumaric acid and alkyl monoesters, comprising from 1 to 4 carbon atoms, of maleic or fumaric acids or anhydrides.

The basic comonomers may be chosen, for instance, from aminoethyl, butylaminoethyl, N,N'-dimethylaminoethyl, and N-tert-butylaminoethyl methacrylates.

The copolymers whose CTFA (4th edition, 1991) name is octylacryl-amide/acrylates/butylaminoethyl methacrylate copolymer, such as the products sold under the name Amphomer® and Lovocryl® 47 by the company National Starch, may also be used.

(3) crosslinked and acylated polyamino amides partially or totally derived from polyamino amides of formula (XVII):

$$-[CO-R_{10}-CO-Z]-\quad\quad\quad (XVII)$$

wherein $R_{10}$ is chosen from divalent groups derived from a saturated dicarboxylic acid, mono- or dicarboxylic aliphatic acids containing an ethylenic double bond, esters of a lower alkanol, comprising from 1 to 6 carbon atoms, of these acids, and groups derived from the addition of any one of said acids to a bis(primary) or bis(secondary) amine, and Z is a group derived from a bis(primary), mono- or bis(secondary) polyalkylene-polyamines and in at least one embodiment comprises:

a) in an amount ranging from 60 to 100 mol %, the group:

$$-NH-[(CH_2)_x-NH-]_p\quad\quad\quad (XVIII)$$

where x=2 and p=2 or 3, or alternatively x=3 and p=2 this group being derived from diethylenetriamine, from triethylenetetraamine, or from dipropylenetriamine;

b) in an amount ranging from 0 to 40 mol %, the group (XVIII) above in which x=2 and p=1 and which is derived from ethylenediamine, or the group derived from piperazine:

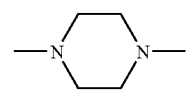

c) in an amount ranging from 0 to 20 mol %, the —NH (CH$_2$)$_6$—NH— group derived from hexamethylenediamine, these polyamino amides being crosslinked by addition reaction of a difunctional crosslinking agent chosen from epihalohydrins, diepoxides, dianhydrides, and bis-unsaturated derivatives, using from 0.025 to 0.35 mol of crosslinking agent per amine group of the polyamino amide and acylated by the action of at least one entity chosen from acrylic acid, chloroacetic acid, alkane sultones, and salts thereof.

The saturated carboxylic acids may be chosen, for example, from acids comprising from 6 to 10 carbon atoms, such as adipic acid, 2,2,4-trimethyladipic acid and 2,4,4-trimethyladipic acid, terephthalic acid, and acids containing an ethylenic double bond such as acrylic acid, methacrylic acid, and itaconic acid.

The alkane sultones used in the acylation may be chosen, for instance, from propane sultone and butane sultone, and the salts of the acylating agents may be chosen, for example, from sodium and potassium salts.

(4) polymers comprising zwitterionic units of formula:

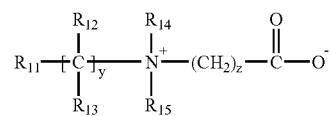

wherein $R_{11}$ is chosen from polymerizable unsaturated groups such as acrylate, methacrylate, acrylamide, and methacrylamide groups, y and z are chosen from integer ranging from 1 to 3, $R_{12}$ and $R_{13}$, which may be identical or different, are chosen from hydrogen, methyl groups, ethyl groups, and propyl groups, and $R_{14}$ and $R_{15}$, which may be identical or different, are chosen from hydrogen and alkyl groups such that the sum of the carbon atoms in $R_{14}$ and $R_{15}$ does not exceed 10.

The polymers comprising such units may also comprise units derived from nonzwitterionic monomers such as dimethyl- or diethylaminoethyl acrylate and methacrylate and alkyl acrylates and methacrylates, acrylamides and methacrylamides and vinyl acetate.

For example, the copolymers of methyl methacrylate/methyl dimethylcarboxymethylammonioethyl methacrylate such as the product sold under the name DIAFORMER Z301 by the company Sandoz may be used.

(5) polymers derived from chitosan comprising monomer units corresponding to formulas (D)-(F):

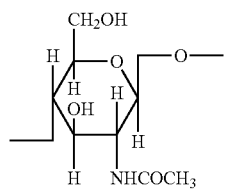
(D)

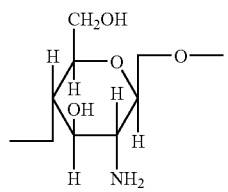
(E)

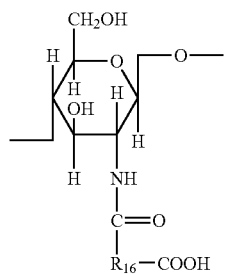
(F)

wherein the unit (D) is present in an amount ranging from 0 to 30%, the unit (E) is present in an amount ranging from 5 to 50%, and the unit (F) is present in an amount ranging from 30% to 90%, it being understood that, in this unit (F), $R_{16}$ is chosen from groups of formula:

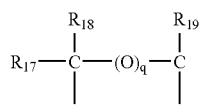

wherein, if q=0, $R_{17}$, $R_{18}$, and $R_{19}$, which may be identical or different, are chosen from hydrogen, methyl residues, hydroxyl residues, acetoxy residues, amino residues, monoalkylamine residues, and dialkylamine residues that are optionally interrupted by at least one nitrogen atom and/or optionally substituted with at least one group chosen from amine, hydroxyl, carboxyl, alkylthio, and sulfonic groups, and alkylthio residues in which the alkyl group bears an amino residue, at least one of the groups $R_{17}$, $R_{18}$ and $R_{19}$ being, in this case, a hydrogen atom;

or, if q=1, $R_{17}$, $R_{18}$, and $R_{19}$ are hydrogen, as well as the acid and base addition salts thereof.

(6) polymers of formula (XIX), such as those described, for example, in French Pat. No. 1 400 366:

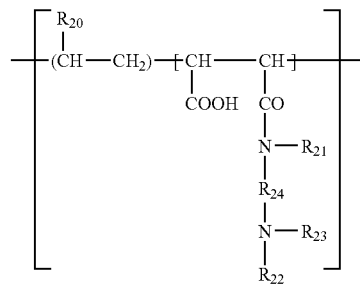
(XIX)

wherein $R_{20}$ is chosen from hydrogen, $CH_3O$, $CH_3CH_2O$, and phenyl groups, $R_{21}$ is chosen from hydrogen and lower alkyl groups such as methyl and ethyl, $R_{22}$ is chosen from hydrogen and $C_{1-6}$ lower alkyl groups such as methyl and ethyl, $R_{23}$ is chosen from $C_{1-6}$ lower alkyl groups such as methyl and ethyl and groups of formula: —$R_{24}$—$N(R_{22})_2$, wherein $R_{24}$ is chosen from —$CH_2$—$CH_2$—, —$CH_2$—$CH_2$—$CH_2$—, and —$CH_2$—$CH(CH_3)$— groups, and $R_{22}$ is defined above, (7) polymers derived from the N-carboxyalkylation of chitosan, such as N-carboxymethylchitosan and N-carboxybutylchitosan sold under the name EVALSAN by the company Jan Dekker.

(8) amphoteric polymers of the type -D-X-D-X— chosen from:

a) polymers obtained by the action of chloroacetic acid or sodium chloroacetate on compounds comprising at least one unit of formula (XX):

(XX)

where D is a group

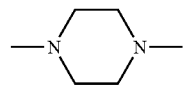

and X is chosen from the symbol E and E' wherein E and E', which may be identical or different, are chosen from divalent groups that are alkylene groups with a straight or branched chains comprising up to 7 carbon atoms in the main chain, which is unsubstituted or substituted with hydroxyl groups and which may comprise, in addition to the oxygen, nitrogen, and sulfur atoms, 1 to 3 aromatic and/or heterocyclic rings; the oxygen, nitrogen and sulfur atoms being present in the form of ether, thioether, sulfoxide, sulfone, sulfonium, alkylamine, alkenylamine groups, hydroxyl, benzylamine, amine oxide, quaternary ammonium, amide, imide, alcohol, ester, and/or urethane groups b) polymers of formula (XXI'):

(XXI')

where D is a group

and X is chosen from the symbols E and E' and at least once E'; E having the meaning given above and E' being chosen from divalent groups that are alkylene groups with a straight or branched chains comprising up to 7 carbon atoms in the main chain, which may be unsubstituted or substituted with at least one hydroxyl group and containing at least one nitrogen atom, the nitrogen atom being substituted with an alkyl chain that is optionally interrupted by an oxygen atom and comprising at least one function chosen from carboxyl functions and hydroxyl functions and betainized by reaction with chloroacetic acid and sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers may also comprise other vinyl comonomers such as vinylcaprolactam.

According to at least one embodiment, the amphoteric fixing polymers may be chosen from those of family (3), such as the copolymers whose CTFA name is octylacryl-amide/acrylates/butylaminoethyl methacrylate copolymer, such as the products sold under the names Amphomer®, Amphomer® LV 71, and Lovocryl® 47 by the company National Starch and those of family (4) such as the copolymers of methyl methacrylate/methyl dimethylcarboxymethylammonioethyl methacrylate, sold, for example, under the name Diaformer® Z301 by the company Sandoz.

Nonionic Fixing Polymers

The nonionic fixing polymers that may be used according to the present disclosure may be chosen, for example, from:
  polyalkyloxazolines;
  vinyl acetate homopolymers;
  vinyl acetate copolymers, for instance, copolymers of vinyl acetate and of acrylic ester; copolymers of vinyl acetate and of ethylene; and copolymers of vinyl acetate and of maleic ester, for example, of dibutyl maleate;
  homopolymers and copolymers of acrylic esters, for instance, copolymers of alkyl acrylates and of alkyl methacrylates, such as the products sold by the company Rohm & Haas under the names Primal® AC-261 K and Eudragit® NE 30 D, by the company BASF under the name 8845, and by the company Hoechst under the name Appretan® N9212;
  copolymers of acrylonitrile and of a nonionic monomer chosen, for example, from butadiene and alkyl (meth) acrylates, for instance, the products sold under the name CJ 0601 B by the company Rohm & Haas;
  styrene homopolymers;
  styrene copolymers, for instance copolymers of styrene and of an alkyl (meth)acrylate, such as the products Mowilith® LDM 6911, Mowilith® DM 611, and Mowilith® LDM 6070 sold by the company Hoechst, and the products Rhodopase® SD 215 and Rhodopas® DS 910 sold by the company Rhodia Chimie; copolymers of styrene, of alkyl methacrylate and of alkyl acrylate; copolymers of styrene and of butadiene; or copolymers of styrene, of butadiene and of vinylpyridine;
  polyamides;
  vinyllactam homopolymers other than vinylpyrrolidone homopolymers, such as the polyvinylcaprolactam sold under the name Luviskol® Plus by the company BASF; and
  vinyllactam copolymers such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37, and VA 28 by the company BASF; and poly(vinylpyrrolidone/vinyl acetate/vinyl propionate) terpolymers, for instance the product sold under the name Luviskol® VAP 343 by the company BASF.

The alkyl groups of the nonionic polymers mentioned above may comprise from 1 to 6 carbon atoms.

Functionalized or non-functionalized, silicone or non-silicone, cationic, nonionic, anionic, or amphoteric polyurethanes and mixtures thereof may also be used as fixing polymers.

The polyurethanes may be chosen, for example, from those disclosed European Pat. Nos. 0 751 162, 0 637 600, 0 648 485, 0 656 021, and 0 619 111, and French Pat. No. 2 743 297, and International Patent Application Publication No. WO 94/03510.

Polyurethanes that are suitable for the present disclosure may include, for instance, the products sold under the names Luviset Pur® and Luviset® Si-Pur by the company BASF.

The at least one additional fixing polymer may be present in the cosmetic composition according to the present disclosure in an amount ranging from 0.01% to 20% by weight, for example, from 0.05% to 15% by weight, or from 0.1% to 10% by weight relative to the total weight of the cosmetic composition.

The cosmetic composition according to the present disclosure may also comprise at least one fixing polymer, also known as a "rheology modifier".

The rheology modifiers may be chosen from fatty acid amides (coconut diethanolamide and monoethanolamide, and oxyethylenated monoethanolamide of carboxylic acid alkyl ether), cellulose-based thickeners (hydroxyethylcellulose, hydroxypropylcellulose and carboxymethylcellulose), guar gum and its derivatives (hydroxypropyl guar), gums of microbial origin (xanthan gum and scleroglucan gum), crosslinked homopolymers of acrylic acid or of acrylamidopropanesulfonic acid, and associative polymers such as those described below other than the polymers of the present disclosure.

The associative polymers that may be used in the cosmetic composition according to the present disclosure may be chosen from water-soluble polymers capable, in an aqueous medium, of reversibly combining with each other or with other molecules.

Their chemical structure may comprise hydrophilic zones and hydrophobic zones characterized by at least one fatty chain.

The associative polymers that may be used according to the present disclosure may be chosen from anionic, cationic, amphoteric, and nonionic polymers.

Non-limiting examples of suitable anionic associative polymers include:
  (I) those comprising at least one hydrophilic unit and at least one fatty-chain allyl ether unit, such as those whose hydrophilic unit comprises an ethylenic unsaturated anionic monomer, for example, of a vinylcarboxylic acid or of an acrylic acid or a methacrylic acid or mixtures thereof, the fatty-chain allyl ether unit of which corresponds to the monomer of formula (XXII):

$$CH_2=CR'CH_2OB_nR \qquad (XXII)$$

wherein R' is chosen from H and $CH_3$, B is an ethyleneoxy radical, n is an integer ranging from 0 to 100, R is a hydrocarbon-based radical chosen from alkyl, arylalkyl, aryl, alkylaryl, and cycloalkyl radicals, comprising from 8 to 30 carbon atoms, for example, from 10 to 24 carbon atoms, or from 12 to 18 carbon atoms. In at least one embodiment, in the unit of formula (XXII), R' is H, n is equal to 10, and R is a stearyl ($C_{18}$) radical.

Anionic associative polymers of this type are described and prepared, according to an emulsion polymerization process, for example, in European Pat. No. 0 216 479.

Examples of these anionic associative polymers include, but are not limited to, polymers formed from 20% to 60% by weight of acrylic acid and/or of methacrylic acid, from 5% to 60% by weight of lower alkyl (meth)acrylates, from 2% to 50% by weight of fatty-chain allyl ether of formula (XXII), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate, and methylenebisacrylamide.

According to at least one embodiment, the polymers may be chosen from crosslinked terpolymers of methacrylic acid, of ethyl acrylate, and of polyethylene glycol (10 EO) stearyl alcohol ether (Steareth-10), for example, those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of $(C_{10}$-$C_{30})$alkyl ester of unsaturated carboxylic acid type.

For example, these polymers are chosen from those in which the hydrophilic unit of unsaturated olefinic carboxylic acid type corresponds to the monomer of formula (XXIII):

wherein $R_1$ is chosen from H, $CH_3$, and $C_2H_5$, that is to say acrylic acid, methacrylic acid, or ethacrylic acid units, respectively, and in which the hydrophobic unit of $(C_{10}$-$C_{30})$alkyl ester of unsaturated carboxylic acid type corresponds to the monomer of formula (XXIV):

wherein $R_2$ is chosen from H, $CH_3$, and $C_2H_5$ (that is to say acrylate, methacrylate, or ethacrylate units, respectively) and in at least one embodiment, H (acrylate units) or $CH_3$ (methacrylate units), $R_3$ denoting a $C_{10}$-$C_{30}$, for example, $C_{12}$-$C_{22}$, alkyl radical.

$(C_{10}$-$C_{30})$ alkyl esters of unsaturated carboxylic acids according to the present disclosure include, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Anionic polymers of this type are described and prepared, for example, according to U.S. Pat. Nos. 3,915,921 and 4,509,949.

Examples of anionic associative polymers of this type that will be used include, but are not limited to, polymers formed from a monomer mixture comprising:

(i) acrylic acid, (ii) an ester of formula (XXIV) described above wherein $R_2$ is chosen from H and $CH_3$, $R_3$ is an alkyl radical comprising from 12 to 22 carbon atoms, and (iii) a crosslinking agent, which is a well-known copolymerizable unsaturated polyethylenic monomer, for instance diallyl phthalate, allyl (meth)acrylate, divinylbenzene, (poly)ethylene glycol dimethacrylate, and methylenebisacrylamide.

The anionic associative polymers of this type may be chosen, for example, from those comprising from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those comprising from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Non-limiting examples of commercial products corresponding to the above polymers include the products sold by the company Goodrich under the trade names Pemulen TR1®, Pemulen TR2®, and Carbopol 1382® and the product sold by the company SEPPIC under the name Coatex SX®. In at least one embodiment, the polymer is Pemulen TR1®.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(IV) acrylic terpolymers comprising:

(a) about 20% to 70% by weight of a carboxylic acid containing α,β-monoethylenic unsaturation, (b) about 20% to 80% by weight of a non-surfactant monomer containing α,β-monoethylenic unsaturation other than (a), (c) about 0.5% to 60% by weight of a nonionic monourethane which is the product of reaction of a monohydric surfactant with a monoisocyanate containing monoethylenic unsaturation, such as those described in European Patent Application No. 0 173 109, such as the terpolymer described in Example 3, a methacrylic acid/methyl acrylate/behenyl alcohol dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

In at least one embodiment, these compounds also comprise as monomer an ester of a carboxylic acid containing α,β-monoethylenic unsaturation and of a $C_1$-$C_4$ alcohol.

A non-limiting example of a compound of this type is Aculyn 22® sold by the company Rohm & Haas, which is a methacrylic acid/ethyl acrylate/stearyl methacrylate oxyalkylenated terpolymer.

Catioinc associative polymers may include, but are not limited to:

(I) cationic associative polyurethanes described in French Patent Application No. 00/09609; now French Pat. No. 2,811,993, and represented by formula (XXV):

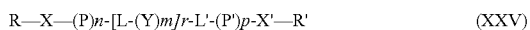

wherein:

R and R', which may be identical or different, are chosen from hydrophobic groups and hydrogen;

X and X', which may be identical or different, are chosen from groups comprising an amine function optionally bearing a hydrophobic group, and L" groups;

L, L', and L", which may be identical or different, are groups derived from diisocyanate;

P and P', which may be identical or different, are groups comprising an amine function optionally bearing a hydrophobic group;

Y is a hydrophilic group;

r is an integer ranging from 1 to 100, for example, from 1 to 50, or from 1 to 25;

n, m, and p, which may be identical or different, are numbers ranging from 0 to 1000; and the molecule contains at least one protonated or quaternized amine function and at least one hydrophobic group.

According to one embodiment, the only hydrophobic groups of these polyurethanes are the groups R and R' at the chain ends.

According to another embodiment, the cationic associative polyurethanes are chosen from those of formula (XXV) wherein:

R and R', which may be identical or different, are chosen from hydrophobic groups, X and X' are L", n and p, which may be identical or different are numbers ranging from 1 to 1 000, and L, L', L", P, P', Y and m have the meanings given above.

In a further embodiment, the cationic associative polyurethanes may be chosen from those of formula (XXV) wherein:

R and R', which may be identical or different, are chosen from hydrophobic groups, X and X' are L", n and p are 0, and L, L', L", Y and m have the meaning given above.

When n and p are 0 these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e., compounds of the type RQ or R'Q, in which R and R' are as defined above and Q is a leaving group such as a halide, a sulfate, etc.

In yet another embodiment, the cationic associative polyurethanes may be chosen from those of formula (XXV), wherein:

R and R', which may be identical or different, are chosen from hydrophobic groups, X and X', which may be identical or different, are chosen from groups comprising a quaternary amine, n and p are 0, and L, L', Y, and m have the meaning given above.

The number-average molecular mass of the cationic associative polyurethanes may range from 400 to 500 000, for example, from 1000 to 400 000, or from 1000 to 300 000.

As used herein, the expression "hydrophobic group" means a radical or polymer containing a saturated or unsaturated, linear or branched hydrocarbon-based chain, which may comprise at least one hetero atom such as P, O, N, and S, or a radical containing a perfluoro or silicone chain. When the hydrophobic group denotes a hydrocarbon-based radical, it comprises at least 10 carbon atoms, for example, from 10 to 30 carbon atoms, from 12 to 30 carbon atoms, or from 18 to 30 carbon atoms.

In at least one embodiment, the hydrocarbon-based group is derived from a monofunctional compound.

For example, the hydrophobic group may be derived from a fatty alcohol such as stearyl alcohol, dodecyl alcohol, and decyl alcohol. It may also be a hydrocarbon-based polymer, for example, polybutadiene.

When X and/or X' denotes a group comprising a tertiary or quaternary amine, X and/or X' may represent one of the following formulas:

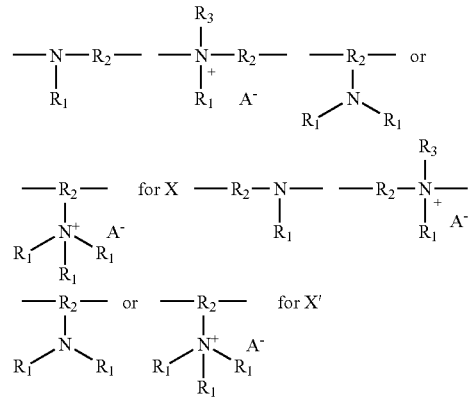

wherein:

$R_2$ is chosen from linear or branched alkylene radicals comprising from 1 to 20 carbon atoms, optionally comprising a saturated or unsaturated ring, and arylene radicals, at least one of the carbon atoms possibly being replaced with a hetero atom chosen from N, S, O, and P;

$R_1$ and $R_3$, which may be identical or different, are chosen from linear or branched $C_1$-$C_{30}$ alkyl or alkenyl radicals and aryl radicals, at least one of the carbon atoms possibly being replaced with a hetero atom chosen from N, S, O, and P; and $A^-$ is a physiologically acceptable counterion.

The groups L, L', and L" are chosen from groups of formula:

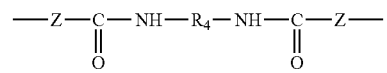

wherein:

Z is chosen from —O—, —S—, and —NH—; and $R_4$ is chosen from linear or branched alkylene radicals comprising from 1 to 20 carbon atoms, optionally comprising a saturated or unsaturated ring, or an arylene radical, at least one of the carbon atoms possibly being replaced with a hetero atom chosen from N, S, O, and P.

The groups P and P' comprising an amine function may be chosen from groups of at least one of the following formulas:

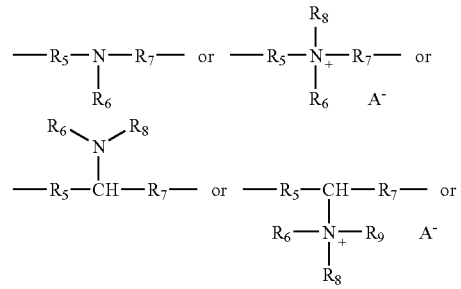

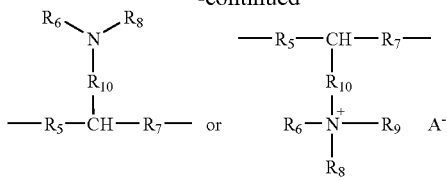

wherein:

$R_5$ and $R_7$ have the same meanings as $R_2$ defined above;

$R_6$, $R_8$, and $R_9$ have the same meanings as $R_1$ and $R_3$ defined above;

$R_{10}$ is a linear or branched, optionally unsaturated alkylene group possibly containing at least one hetero atom chosen from N, O, S, and P; and $A^-$ is a physiologically acceptable counterion.

As used herein with respect to the meaning of Y, the term "hydrophilic group" means a polymeric or non-polymeric water-soluble group.

By way of example, when it is not a polymer, it may be chosen, for instance, from ethylene glycol, diethylene glycol, and propylene glycol.

When it is a hydrophilic polymer, in accordance with one embodiment, it may be chosen, for example, from polyethers, sulfonated polyesters, sulfonated polyamides, and mixtures of these polymers. In at least one embodiment, the hydrophilic compound is a polyether, for example, poly(ethylene oxide) and poly(propylene oxide).

The cationic associative polyurethanes of formula (XXV) that may be used according to the present disclosure may be formed from diisocyanates and from various compounds with functions containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes which can be used according to the present disclosure" encompasses these three types of polymer, namely polyurethanes per se, polyureas and polythioureas, and also copolymers thereof.

A first type of compound that may be involved in the preparation of the polyurethane of formula (XXV) is a compound comprising at least one unit containing an amine function. This compound may be multifunctional, and in at least one embodiment, the compound is difunctional, that is to say that, according to one embodiment, this compound comprises two labile hydrogen atoms borne, for example, by a function chosen from hydroxyl, primary amine, secondary amine, and thiol functions. A mixture of multifunctional and difunctional compounds in which the percentage of multifunctional compounds is low may also be used.

As mentioned above, this compound may comprise more than one unit containing an amine function. In this case, it may be a polymer bearing a repetition of the unit containing an amine function.

Compounds of this type may be chosen from those of the following formulas:

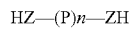

and

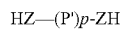

wherein Z, P, P', n, and p are as defined above.

Examples of compounds containing an amine function include, but are not limited to, N-methyldiethanolamine, N-tert-butyldiethanolamine and N-sulfoethyldiethanolamine.

A second compound which may be involved in the preparation of the polyurethane of formula (XXV) is a diisocyanate corresponding to the formula:

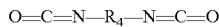

in which $R_4$ is as defined above.

Example of such compounds include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate.

A third compound which may be involved in the preparation of the polyurethane of formula (XXV) is a hydrophobic compound intended to form the terminal hydrophobic groups of the polymer of formula (XXV).

This compound may comprise a hydrophobic group and a function containing a labile hydrogen, for example hydroxyl, primary or secondary amine, and thiol functions.

For example, this compound may be a fatty alcohol such as stearyl alcohol, dodecyl alcohol, and decyl alcohol. When this compound comprises a polymeric chain, it may be, for example, α-hydroxylated hydrogenated polybutadiene.

The hydrophobic group of the polyurethane of formula (XXV) may also result from the quaternization reaction of the tertiary amine of the compound comprising at least one tertiary amine unit. Thus, the hydrophobic group is introduced via the quaternizing agent. This quaternizing agent may be a compound of the type RQ or R'Q, in which R and R' are as defined above and Q is a leaving group such as a halide, a sulfate, etc.

The cationic associative polyurethane may also comprise at least one hydrophilic block. This block may be provided by a fourth type of compound involved in the preparation of the polymer. This compound may be multifunctional, and in at least one embodiment, it is difunctional. It is also possible to have a mixture in which the percentage of multifunctional compound is low.

The functions containing a labile hydrogen may include, for example, alcohol, primary or secondary amine, and thiol functions. This compound may be a polymer terminated at the chain ends with one of these functions containing a labile hydrogen.

The hydrophilic group termed Y in formula (XXV) is optional. In other words, the units containing a quaternary amine or protonated function may suffice to provide the solubility or water-dispersibility required for this type of polymer in an aqueous solution.

Although the presence of a hydrophilic group Y is optional, in at least one embodiment, the cationic associative polyurethanes comprise such a group.

(II) quaternized cellulose derivatives and polyacrylates containing non-cyclic amine side groups.

The quaternized cellulose derivatives may include, for example:

quaternized celluloses modified with groups comprising at least one fatty chain, such as alkyl, arylalkyl, and alkylaryl groups comprising at least 8 carbon atoms, and mixtures thereof; and quaternized hydroxyethylcelluloses modified with groups comprising at least one fatty chain, such as alkyl, arylalkyl, and alkylaryl groups comprising at least 8 carbon atoms, and mixtures thereof.

The alkyl radicals borne by the above quaternized celluloses or hydroxyethylcelluloses may comprise from 8 to 30 carbon atoms. In at least one embodiment, the aryl radicals may be chosen from phenyl, benzyl, naphthyl, and anthryl groups.

Examples of quaternized alkylhydroxyethylcelluloses containing $C_8$-$C_{30}$ fatty chains include, for instance, the products Quatrisoft LM 200®, Quatrisoft LM-X 529-18-A®, Quatrisoft LM-X 529-18B® ($C_{12}$ alkyl), and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

The amphoteric associative polymers may be chosen, for example, from those comprising at least one non-cyclic cationic unit. In at least one embodiment, the amphoteric associative polymers are chosen from those prepared from or comprising 1 to 20 mol %, for example, from 1.5 to 15 mol %, or from 1.5 to 6 mol % of fatty-chain monomer relative to the total number of moles of monomers.

According to another embodiment, the amphoteric associative polymers may comprise or are prepared by copolymerizing:

1) at least one monomer chosen from those of formulas (XXVI) and (XXVII):

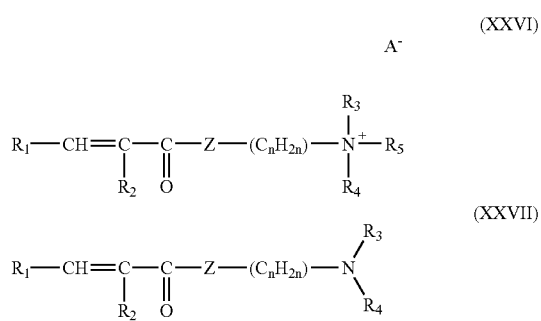

wherein $R_1$ and $R_2$, which may be identical or different, are chosen from hydrogen and methyl radicals, $R_3$, $R_4$, and $R_5$, which may be identical or different, are chosen from linear or branched alkyl radicals comprising from 1 to 30 carbon atoms, Z is chosen from NH and oxygen, n is an integer ranging from 2 to 5, and $A^-$ is an anion derived from an organic or mineral acid, such as methosulfate anions and halides such as chloride and bromide;

2) at least one monomer of formula (XXVIII)

wherein $R_6$ and $R_7$, which may be identical or different, are chosen from hydrogen and methyl radicals; and 3) at least one monomer of formula (XXIX):

wherein $R_6$ and $R_7$, which may be identical or different, are chosen from hydrogen and methyl radicals, X is chosen from oxygen and nitrogen, and $R_8$ is a linear or branched alkyl radical comprising from 1 to 30 carbon atoms;

wherein at least one of the monomers of formulas (XXVI), (XXVII), and (XXVIII) comprises at least one fatty chain.

The monomers of formulas (XXVI) and (XXVII) of the present disclosure may be chosen, for example, from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, and dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

In one embodiment, the monomer of formula (XXVI) may be chosen from acrylamidopropyltrimethylammonium chloride and methacrylamidopropyltrimethylammonium chloride.

In another embodiment, the monomers of formula (XXVII) may be chosen from acrylic acid, methacrylic acid, crotonic acid, and 2-methylcrotonic acid. In a further-embodiment, the monomer of formula (XXVIII) is acrylic acid.

According to yet another embodiment, the monomers of formula (XXIX) of the present disclosure may be chosen from $C_{12}$-$C_{22}$, for example, $C_{16}$-$C_{18}$, alkyl acrylates and methacrylates.

The monomers constituting the fatty-chain amphoteric polymers of the present disclosure may be neutralized and/or quaternized.

According to at least one embodiment, the ratio of the number of cationic charges/anionic charges may be equal to about 1.

The amphoteric associative polymers according to the present disclosure comprise from 1 mol % to 10 mol % of the monomer comprising a fatty chain (monomer of formula (XXVI), (XXVII) or (XXVIII)), for example, from 1.5 mol % to 6 mol %.

The weight-average molecular weights of the amphoteric associative polymers according to the present disclosure may range from 500 to 50 000 000, for example, from 10 000 to 5 000 000.

The amphoteric associative polymers according to the present disclosure may also contain other monomers such as nonionic monomers, for example, $C_1$-$C_4$ alkyl acrylates and methacrylates.

Amphoteric associative polymers according to the present disclosure are described and prepared, for example, in International Patent Application Publication No. WO 98/44012.

In at least one embodiment, the amphoteric associative polymers according to the present disclosure may be chosen from acrylic acid/(meth)acrylamidopropyltrimethyl-ammonium chloride/stearyl methacrylate terpolymers.

The nonionic associative polymers that may be used according to the present disclosure may be chosen from:

(1) celluloses modified with groups comprising at least one fatty chain;

for example:

hydroxyethylcelluloses modified with groups comprising at least one fatty chain, such as alkyl, arylalkyl, and alkylaryl groups, and mixtures thereof, and in which the alkyl groups are, for example, $C_8$-$C_{22}$, for instance the product Natrosol Plus Grade 330 CS® ($C_{16}$ alkyls) sold by the company Aqualon, and the product Bermocoll EHM 100® sold by the company Berol Nobel, those modified with alkylphenyl polyalkylene glycol ether groups, such as the product Amercell Polymer HM-1500® (nonylphenyl polyethylene glycol(15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

(3) copolymers of vinylpyrrolidone and of fatty-chain hydrophobic monomers; for example:
- the products Antaron V216® or Ganex V216® (vinylpyrrolidone/hexa-decene copolymer) sold by the company I.S.P.
- the products Antaron V220® or Ganex V220® (vinylpyrrolidone/eicosene copolymer) sold by the company I.S.P.

(4) copolymers of $C_1$-$C_6$ alkyl methacrylates or acrylates and of amphiphilic monomers comprising at least one fatty chain, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

In at least one embodiment, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In another embodiment, it is possible for at least one pendent chain to be included. In addition, the polymer may comprise a hydrocarbon-based chain at one end or at both ends of a hydrophilic block.

The polyurethane polyethers may be multiblock, for example, in triblock form. Hydrophobic blocks may be at each end of the chain (for example: triblock copolymer with a hydrophilic central block) or distributed both at the ends and in the chain (for example: multiblock copolymer). These polymers may also be chosen from graft polymers and starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers may comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

Examples of nonionic fatty-chain polyurethane polyethers that may be used include Rheolate 205® containing a urea function, sold by the company Rheox, Rheolate® 208, 204, and 212, and also Acrysol RM 184®.

Polyurethanes may also be chosen, for example, from the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, for example, in water or in aqueous-alcoholic medium. Examples of such polymers include, but are not limited to, Rheolate® 255, Rheolate® 278 and Rheolatee 244 sold by the company Rheox, and the products DW 1206F and DW 1206J sold by the company Rohm & Haas.

The polyurethane polyethers that may be used according to the present disclosure may also include those described in the article by G. Fonnum, J. Bakke and Fk. Hansen—Colloid Polym. Sci., 271, 380-389 (1993).

In at least one embodiment, the polyurethane polyether may be chosen from those that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm & Haas under the names Aculyn 44® and Aculyn 46® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol(39%) and water (26%)].

The at least one additional fixing polymer may be present in the cosmetic composition according to the present disclosure in an amount ranging from 0.01% to 20% by weight, for example, from 0.05% to 10% by weight, or from 0.1% to 10% by weight, relative to the total weight of the composition.

Cosmetic Adjuvants

The cosmetic composition according to the present disclosure may also comprise at least one cosmetic adjuvant chosen from cationic, anionic, amphoteric, or nonionic surfactants, silicones other than those of the present disclosure, conditioning agents of ester type, antifoams, moisturizers, emollients, plasticizers, water-soluble and liposoluble, silicone-based or non-silicone-based sunscreens, permanent or temporary dyes, fragrances, peptizers, preserving agents, ceramides, pseudoceramides, vitamins and provitamins, including panthenol, proteins, sequestrants, solubilizers, basifying agents, anticorrosion agents, fatty substances such as plant, animal, mineral and synthetic oils, reducing agents, antioxidants, and oxidizing agents.

It is to be understood that a person skilled in the art will take care to select the optional adjuvants and the amount thereof such that they do not harm the properties of the compositions of the present disclosure.

The at least one cosmetic adjuvant may be present in the composition in an amount ranging from 0.001% to 50% by weight relative to the total weight of the composition.

Cosmetically Acceptable Medium

As used herein, the term "cosmetically acceptable medium" means a medium that is compatible with keratin materials such as the hair.

The cosmetically acceptable medium may be chosen from alcoholic, aqueous, and aqueous-alcoholic mediums. Thus, the medium may be chosen from water, at least one alcohol, and mixtures of water and of at least one cosmetically acceptable solvent such as $C_1$-$C_4$ lower alcohols, polyol monoethers, and mixtures thereof. In at least one embodiment, the alcohol is ethanol.

The cosmetic compositions in accordance with the present disclosure may be in a form chosen from creams, mousses, gels, and hair conditioners.

According to one embodiment, the composition according to the present disclosure is in the form of a gel with a viscosity of at least 500 cps, measured at 25° C. with a Thermoelectron RS600 rheometer at a shear rate of 1 s$^{-1}$.

The cosmetic composition may generally have a viscosity ranging from 500 to 500 000 cps at 25° C., for example, from 500 to 100 000 cps at 25° C., or from 500 to 50 000 cps at 25° C., at a shear rate of 1 s$^{-1}$ which can be measured using a RS600 rheometer from Thermoelectron.

The cosmetic compositions in accordance with the present disclosure may also be packaged in a pump-dispenser bottle or in an aerosol device that is common in cosmetics.

The propellants used in the aerosol systems according to the present disclosure may be chosen from air, nitrogen, carbon dioxide, dimethyl ether, $C_3$ to $C_5$ alkanes, 1,1-difluoroethane, and mixtures thereof.

Also disclosed herein is an aerosol device comprising the compositions described above and a means for distributing this composition.

Further disclosed herein is a cosmetic process for treating, for example styling, the hair, comprising applying an effective amount of a composition described above to wet or dry hair, and optionally rinsing the hair after an optional leave-in time or after optional drying.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLE

Composition (A) in accordance with the present disclosure was prepared from the following compounds:

| Composition A | |
|---|---|
| Styleze W20 [1] | 2% |
| Cetyl alcohol | 4% |
| Glycerol | 5% |
| Amodimethicone | 1.5% |
| Cetyltrimethylammonium chloride | 1% |
| Hydroxypropyl guar | 1% |
| Glyceryl stearate | 1% |
| Polyvinylpyrrolidone | 3% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

Composition (B) in accordance with the present disclosure was prepared from the following compounds:

| Composition B | |
|---|---|
| Styleze W20 [1] | 5% |
| Cetearyl alcohol | 4% |
| Glycerol | 10% |
| Amodimethicone | 1.5% |
| Behenyltrimethylammonium chloride | 1% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

Composition (C) in accordance with the present disclosure was prepared from the following compounds:

| Composition C | |
|---|---|
| Styleze W20 [1] | 4% |
| Cetearyl alcohol | 4% |
| Glycerol | 5% |
| Amodimethicone | 2% |
| Behenyltrimethylammonium chloride | 1.5% |
| Laureth-4 | 0.5% |
| Mineral oil | 2% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

Composition (D) in accordance with the present disclosure was prepared from the following compounds:

| Composition D | |
|---|---|
| Styleze W20 [1] | 0.5% |
| Cetyl alcohol | 4% |
| Glycerol | 3% |
| Cetyltrimethylammonium chloride | 1% |
| Dimethiconol | 2% |
| Preserving agents | qs % |
| Water | qs 100% |

[1] Vinylpyrrolidone/dimethylaminopropylmethacrylamide/lauryldimethylmethacrylamidopropylammonium chloride terpolymer, sold by the company ISP under the name Styleze W20

The percentages of each of the compounds in the cosmetic compositions according to the present disclosure are calculated by weight of active material relative to the total weight of the composition.

Compositions (A) to (D) were applied to European hair.

It was observed that the compositions in accordance with the present disclosure had both good spreading properties and satisfactory viscosity.

These cosmetic compositions likewise made it possible to tame the hair in a satisfactory manner.

What is claimed is:

1. A cosmetic composition for treating keratin fibers, comprising, in a cosmetically acceptable medium:
   (i) at least one cationic poly(vinyllactam) polymer comprising:
      a) at least one monomer chosen from vinyllactam and alkylvinyllactam monomers;
      b) at least one monomer chosen from monomers of formulas (Ia) and (Ib):

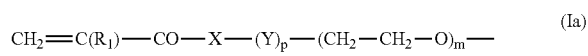

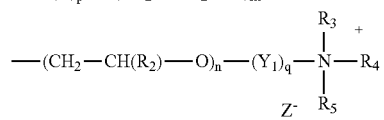

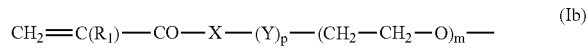

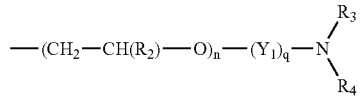

wherein:

X is chosen from oxygen and $NR_6$ radicals, $R_1$ and $R_6$, which may be identical or different, are chosen from hydrogen and linear or branched $C_1$-$C_5$ alkyl radicals, $R_2$ is chosen from linear or branched $C_1$-$C_4$ alkyl radicals, $R_3$, $R_4$ and $R_5$, which may be identical or different, are chosen from hydrogen, linear or branched $C_1$-$C_{30}$ alkyl radicals, and radicals of formula (II):

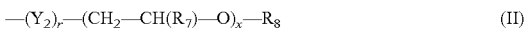

Y, $Y_1$ and $Y_2$, which may be identical or different, are chosen from linear or branched $C_2$-$C_{16}$ alkylene radicals, $R_7$ is chosen from hydrogen, linear or branched $C_1$-$C_4$ alkyl radicals, and linear or branched $C_1$-$C_4$ hydroxyalkyl radicals, $R_8$ is chosen from hydrogen and linear or branched $C_1$-$C_{30}$ alkyl radicals, p, q and r, which may be identical or different, are equal to 0 or 1, m and n, which may be identical or different, are chosen from integers ranging from 0 to 100, x is an integer ranging from 1 to 100, and Z is an organic or mineral acid anion;

with the proviso that:

at least one of the substituents $R_3$, $R_4$, $R_5$, or $R_8$ is a linear or branched $C_9$-$C_{30}$ alkyl radicals, if m or n is other than zero, then q is equal to 1, and if m or n is equal to zero, then p or q is equal to 0;

(ii) cetearyl alcohol, and (iii) at least one polyol with a molecular weight of greater than 80.

2. The cosmetic composition of claim 1, wherein the at least one monomer chosen from vinyllactam and alkylvinyllactam monomers is chosen from compounds of structure (III):

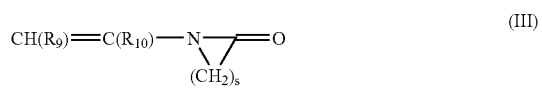

wherein:

s is an integer ranging from 3 to 6, $R_9$ is chosen from hydrogen and $C_1$-$C_5$ alkyl radicals, $R_{10}$ is chosen from hydrogen and $C_1$-$C_5$ alkyl radicals, with the proviso that at least one of the radicals $R_9$ and $R_{10}$ is hydrogen.

3. The cosmetic composition of claim 2, wherein the monomer of structure (III) is vinylpyrrolidone.

4. The cosmetic composition of claim 1, wherein in formula (Ia) and/or (Ib), the radicals $R_3$, $R_4$ and $R_5$, which may be identical or different, are chosen from hydrogen and linear or branched $C_1$-$C_{30}$ alkyl radicals.

5. The cosmetic composition of claim 1, wherein the at least one monomer b) is a monomer of formula (Ia).

6. The cosmetic composition of claim 5, wherein, in formula (Ia), m and n are equal to zero.

7. The cosmetic composition according to claim 1, wherein the counterion $Z^-$ of the monomers of formula (Ia) is chosen from halide ions, phosphate ions, the methosulfate ion, and the tosylate ion.

8. The cosmetic composition of claim 1, wherein the at least one cationic poly(vinyllactam) polymer comprises at least one additional monomer chosen from cationic and nonionic monomers.

9. The cosmetic composition of claim 8, wherein the cationic poly(vinyllactam) is a terpolymer comprising:
   (a) one monomer of structure (III),
   (b) one monomer of formula (Ia) wherein p=1, q=0, $R_3$ and $R_4$, which may be identical or different, are chosen from hydrogen and $C_1$-$C_5$ alkyl radicals, and $R_5$ is a $C_9$-$C_{24}$ alkyl radical, and
   (c) one monomer of formula (Ib) wherein $R_3$ and $R_4$, which may be identical or different, are chosen from hydrogen and $C_1$-$C_5$ alkyl radicals.

10. The cosmetic composition of claim 9, wherein the terpolymer comprises, by weight 40% to 95% of monomer (a), 0.25% to 50% of monomer (b), and 0.1% to 55% of monomer (c).

11. The composition of claim 1, wherein the at least one cationic poly(vinyllactam) is chosen from vinylpyrrolidone/dimethylaminopropylmethacrylamide/dodecyldimethyl-methacrylamidopropylammonium tosylate terpolymers, vinylpyrrolidone/dimethylaminopropylmethacrylamide/cocoyldimethylmethacrylamidopropylammonium tosylate terpolymers and vinylpyrrolidone/dimethylaminopropylmethacrylamide/lauryldimethylmethacrylamidopropylammonium chloride terpolymers.

12. The composition of claim 1, wherein the at least one cationic poly(vinyllactam) polymer is a vinylpyrrolidone/dimethylaminopropyl methacrylamide/lauryldimethylmethacrylamidopropylammonium chloride terpolymer.

13. The composition of claim 1, wherein the weight-average molecular mass of the at least one cationic poly(vinyllactam) polymer ranges from 500 to 20,000,000.

14. The composition of claim 13, wherein the weight-average molecular mass of the at least one cationic poly (vinyllactam) ranges from 400,000 to 800,000.

15. The cosmetic composition of claim 1, wherein the at least one cationic poly(vinyllactam) is present in the composition in an amount ranging from 0.05% to 30% by weight relative to the total weight of the composition.

16. The cosmetic composition of claim 15, wherein the at least one cationic poly(vinyllactam) is present in the composition in an amount ranging from 0.2% to 10% by weight relative to the total weight of the composition.

17. The cosmetic composition of claim 1, wherein the cetearyl alcohol is present in the composition in an amount ranging from 0.1% to 30% by weight relative to the total weight of the composition.

18. The cosmetic composition of claim 17, wherein the cetearyl alcohol is present in the composition in an amount ranging from 0.5% to 10% by weight relative to the total weight of the composition.

19. The cosmetic composition of claim 1, wherein the at least one polyol has a molecular weight ranging from 90 to 350 and is chosen from compounds of formula (V):

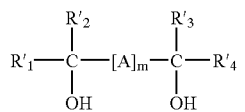
(V)

wherein $R'_1$, $R'_2$, $R'_3$ and $R'_4$, which may be identical or different, are chosen from hydrogen, $C_1$-$C_6$ alkyl radicals, and $C_1$-$C_6$ mono- or polyhydroxyalkyl radicals, A is chosen from linear or branched alkylene radicals comprising from 1 to 18 carbon atoms and from 0 to 9 oxygen atoms, m is equal to 0 or 1.

20. The cosmetic composition of claim 19, wherein the at least one polyol is chosen from polyols of formula (V) in which m=0.

21. The cosmetic composition of claim 20, wherein the at least one polyol is chosen from 1,2,3-propanetriol, pinacol(2,3-dimethyl-2,3-butanediol), 1,2,3-butanetriol, 2,3-butanediol, and sorbitol.

22. The cosmetic composition of claim 21, wherein the at least one polyol is 1,2,3-propanetriol.

23. The cosmetic composition of claim 1, wherein the at least one polyol is present in the composition in an amount ranging from 0.1% to 30% by weight relative to the total weight of the composition.

24. The cosmetic composition of claim 23, wherein the at least one polyol is present in the composition in an amount ranging from 1% to 15% by weight relative to the total weight of the composition.

25. The cosmetic composition of claim 1, further comprising at least one silicone.

26. The cosmetic composition of claim 25, wherein the at least one silicone is an oxyalkylenated silicone chosen from compounds of formulas (VI), (VII), (VIII), (IX), and (X):

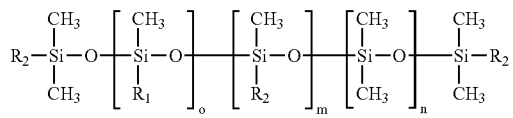
(VI)

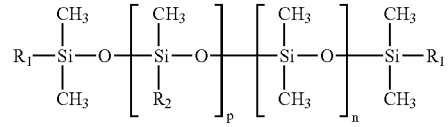
(VII)

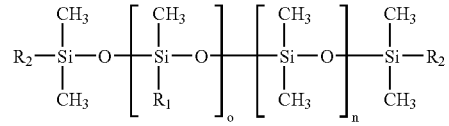
(VIII)

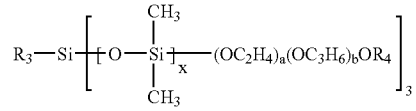
(IX)

wherein:
$R_1$, which may be identical or different, is chosen from linear or branched $C_1$-$C_{30}$ alkyl radicals and phenyl radicals, $R_2$, which may be identical or different, is chosen from —$C_cH_{2c}$—O—$(C_2H_4O)_a(C_3H_6O)_b$—$R_5$ and —$C_cH_{2c}$—O—$(C_4H_8O)_a$—$R_5$, $R_3$ and $R_4$, which may be identical or different, are chosen from linear or branched $C_1$ to $C_{12}$ alkyl radicals, $R_5$, which may be identical or different, is chosen from hydrogen, linear or branched alkyl radicals comprising from 1 to 12 carbon atoms, linear or branched alkoxy radicals comprising from 1 to 6 carbon atoms, linear or branched acyl radical comprising from 2 to 30 carbon atoms, hydroxyl radicals, —$SO_3M$ radicals, $C_1$-$C_6$ aminoalkoxy radicals optionally substituted on the amine, $C_2$-$C_6$ aminoacyl radicals optionally substituted on the amine, —$NHCH_2CH_2COOM$ radicals, —$N(CH_2CH_2COOM)_2$ radicals, aminoalkyl radicals optionally substituted on the amine and on the alkyl chain, $C_2$-$C_{30}$ carboxyacyl radicals, groups optionally substituted with one or two substituted aminoalkyl radicals, —$CO(CH_2)_dCOOM$ radicals, —$COCHR_7(CH_2)_dCOOM$ radicals, —$NHCO(CH_2)_dOH$ radicals, —$NH_3Y$ radicals, and phosphate groups, M, which may be identical or different, is chosen from hydrogen, Na, K, Li, $NH_4$ and organic amines, $R_7$ is chosen from hydrogen and —$SO_3M$ radicals, d is a number ranging from 1 to 10,
m is a number ranging from 0 to 20,
n is a number ranging from 0 to 500,
o is a number ranging from 0 to 20,
p is a number ranging from 1 to 50,
a is a number ranging from 0 to 50,
b is a number ranging from 0 to 50,
a+b is greater than or equal to 2,
c is a number ranging from 0 to 4,
x is a number ranging from 1 to 100,
Y is a monovalent mineral and organic anion,
with the proviso that when the silicone is of formula (VII) and $R_5$ is hydrogen, then n is greater than 12, $([Z(R_2SiO)_qR'_2SiZO][(C_nH_{2n}O)_r])_s$ (X)

wherein in formula (X):
$R_2$ and $R'_2$, which may be identical or different, are chosen from monovalent $C_1$-$C_{30}$ hydrocarbon-based radicals, n is an integer ranging from 2 to 4,
q is a number greater than or equal to 4,
r is a number greater than or equal to 4,
s is a number greater than or equal to 4,
Z is a divalent organic group linked to the adjacent silicon atom via a carbon-silicon bond and to the polyoxyalkylene block ($C_nH_{2n}O$) via an oxygen atom,
the average molecular weight of each siloxane block ranges from 400 to 10,000,
the average molecular weight of each polyoxyalkylene block ranges from 300 to 10,000,
the siloxane blocks are present in the block copolymer in an amount ranging from 10% to 95% by weight of the block copolymer, and
the number-average molecular weight of the block copolymer optionally ranging from 2500 to 1,000,000.

27. The cosmetic composition of claim 26, wherein, in formulas (VI), (VII), (VIII), (IX), and (X),
Y is chosen from halide, sulfate and carboxylate anions,
q is a number from 4 to 100,
r is a number from 5 to 100, and/or
s is a number from 5 to 300.

28. The cosmetic composition of claim 25, wherein the at least one silicone is a silicone gum.

29. The cosmetic composition of claim 28, wherein the at least one silicone gum is chosen from polyorganosiloxanes having number-average molecular masses ranging from 200,000 to 1,000,000, used alone or in the form of a mixture in a solvent.

30. The cosmetic composition of claim 29, wherein the silicone gums are chosen from:
polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane,
mixtures formed from a polydimethylsiloxane hydroxylated at the end of the chain and of a cyclic polydimethylsiloxane;
mixtures formed from a polydimethylsiloxane gum and a cyclic silicone; and
mixtures of polydimethylsiloxanes of different viscosities.

31. The cosmetic composition of claim 25, wherein the at least one silicone is an amino silicone.

32. The cosmetic composition of claim 31, wherein the amino silicone is chosen from:
(a) compounds of formula (XI):

$$(R^1)_a(T)_{3-a}Si[OSi(T)_2]_n\text{-}[OSi(T)_b(R^1)_{2b}]_m\text{—}OSi(T)_{3-a}(R^1)_a$$ (XI)

wherein:
T is chosen from hydrogen, phenyl radicals, hydroxyl radicals, $C_1$-$C_8$ alkyl radicals, and $C_1$-$C_8$ alkoxy radicals, a is an integer from 0 to 3,
b is equal to 0 or 1,
m and n are numbers such that the sum (n+m) ranges from 1 to 2000, wherein n is a number ranging from 0 to 1999, and m is a number ranging from 1 to 2000;
$R^1$ is a monovalent radical of formula —$C_qH_{2q}L$ in which q is a number ranging from 2 to 8 and L is an optionally quaternized amino group chosen from:

—N($R^2$)—$CH_2$—$CH_2$—N($R^2$)$_2$

N($R^2$)$_2$

N$^+$($R^2$)$_3$Q$^-$

N$^+$($R^2$)(H)$_2$Q$^-$

N$^+$($R^2$)$_2$HQ$^-$

N($R^2$)—$CH_2$—$CH_2$N$^+$($R^2$)(H)$_2$Q$^-$ wherein $R^2$ is chosen from hydrogen, phenyl radicals, benzyl radicals, and saturated monovalent hydrocarbon-based radicals, and Q$^-$ is a halide ion;
(b) compounds of formula (XIV):

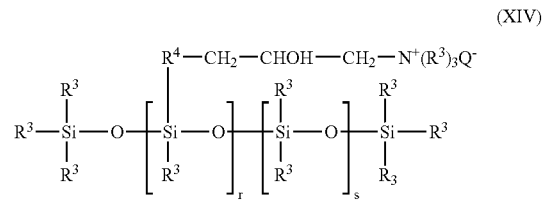
(XIV)

wherein:
$R^3$ is a monovalent $C_1$-$C_{18}$ hydrocarbon-based radical,
$R^4$ is a divalent hydrocarbon-based radical,
Q$^-$ is a halide ion,
r is an average statistical value ranging from 2 to 20; and
s is an average statistical value ranging from 20 to 200;
(c) quaternary ammonium silicones of formula (XV):

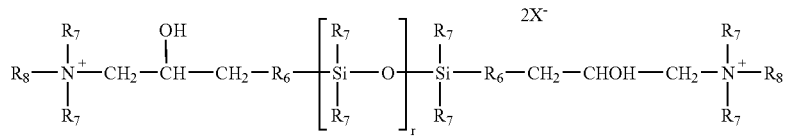
XV wherein:
$R_7$, which may be identical or different, is a monovalent hydrocarbon-based radical comprising from 1 to 18 carbon atoms;
$R_6$ is a divalent hydrocarbon-based radical;
$R_8$, which may be identical or different, is chosen from hydrogen and monovalent hydrocarbon-based radicals comprising from 1 to 18 carbon atoms;
X$^-$ is an anion chosen from halide ions and organic acid salts;
r is a mean statistical value ranging from 2 to 200;

(d) amino silicones of formula (XVI):

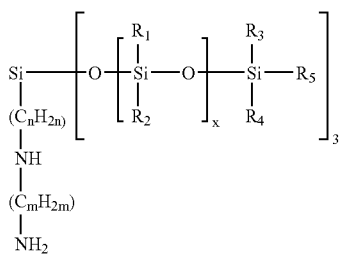

wherein:

$R_1$, $R_2$, $R_3$, and $R_4$, which may be identical or different, are chosen from $C_1$-$C_4$ alkyl radicals and phenyl groups, $R_5$ is chosen from $C_1$-$C_4$ alkyl radicals and hydroxyl groups, n is an integer ranging from 1 to 5, m is an integer ranging from 1 to 5, and x is chosen such that the amine number ranges from 0.01 to 1 meq/g.

33. The cosmetic composition of claim 1, further comprising at least one additional fixing polymer.

34. The cosmetic composition of claim 1, wherein the composition has a viscosity ranging from 500 to 500,000 cps at 25° C. at a shear rate of $1\ s^{-1}$.

35. The cosmetic composition of claim 34, wherein the composition has a viscosity ranging from 500 to 50,000 cps at 25° C. at a shear rate of $1\ s^{-1}$.

36. The cosmetic composition of claim 1, further comprising at least one cosmetic adjuvant chosen from cationic, anionic, amphoteric, or nonionic surfactants, additional silicones, conditioning agents of ester type, antifoams, moisturizers, emollients, plasticizers, water-soluble and liposoluble, silicone-based or non-silicone-based sunscreens, permanent or temporary dyes, fragrances, peptizers, preserving agents, ceramides, pseudoceramides, vitamins and provitamins, proteins, sequestrants, solubilizers, basifying agents, anticorrosion agents, fatty substances, reducing agents, antioxidants, and oxidizing agents.

37. The cosmetic composition according to claim 36, wherein the at least one cosmetic adjuvant is present in the composition in an amount ranging from 0.001% to 50% by weight relative to the total weight of the composition.

38. The cosmetic composition of claim 1, wherein the cosmetically acceptable medium is chosen from aqueous, alcoholic, and aqueous-alcoholic mediums.

39. The cosmetic composition of claim 38, wherein the aqueous-alcoholic medium comprises $C_1$-$C_4$ lower alcohols, polyol monoethers, and mixtures thereof.

40. The cosmetic composition of claim 39, wherein the alcohol is ethanol.

41. The cosmetic composition of claim 1, wherein the composition is in a form chosen from creams, mousses, gels, and hair conditioners.

42. The cosmetic composition of claim 1, wherein the composition is packaged in a device chosen from vaporisers, pump-dispenser bottles, and aerosol devices.

43. The cosmetic composition of claim 42, wherein the composition is packaged in an aerosol device.

44. The cosmetic composition of claim 43, wherein the composition comprises a propellant chosen from air, nitrogen, carbon dioxide, dimethyl ether, $C_3$-$C_5$ alkanes, 1,1-difluoroethane, and mixtures thereof.

45. An aerosol device comprising a container comprising a cosmetic composition and a means for distributing the composition, wherein the cosmetic composition comprises, in a cosmetically acceptable medium:

(i) at least one cationic poly(vinyllactam) polymer comprising:
 a) at least one monomer chosen from vinyllactam and alkylvinyllactam monomers;
 b) at least one monomer chosen from monomers of formulas (Ia) and (Ib):

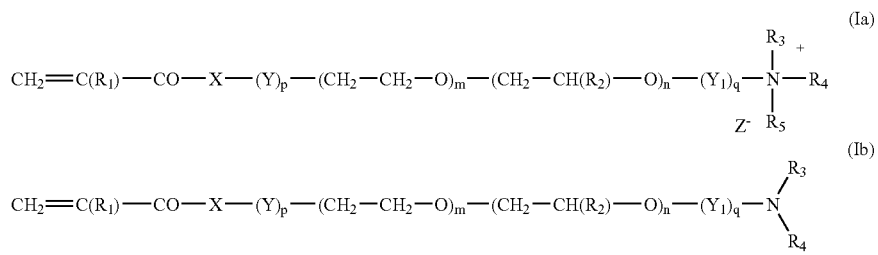

wherein:

X is chosen from oxygen and $NR_6$ radicals, $R_1$ and $R_6$, which may be identical or different, are chosen from hydrogen and linear or branched $C_1$-$C_6$ alkyl radicals, $R_2$ is chosen from linear or branched $C_1$-$C_4$ alkyl radicals, $R_3$, $R_4$, and $R_5$, which may be identical or different, are chosen from hydrogen, linear or branched $C_1$-$C_{30}$ alkyl radicals, and radicals of formula (II):

$$—(Y_2)_r—(CH_2—CH(R_7)—O)_x—R_8 \qquad (II)$$

Y, $Y_1$, and $Y_2$, which may be identical or different, are chosen from linear or branched $C_2$-$C_{16}$ alkylene radicals, $R_7$ is chosen from hydrogen, linear or branched $C_1$-$C_4$ radicals, and linear or branched $C_1$-$C_4$ hydroxyalkyl radicals, $R_8$ is chosen from hydrogen and linear or branched $C_1$-$C_{30}$ alkyl radicals, p, q, and r, which may be identical or different, are equal to 0 or 1, m and n, which may be identical or different, are chosen from integers ranging from 0 to 100, x is an integer ranging from 1 to 100, Z is an organic or mineral acid anion, with the proviso that:

at least one of the substituents $R_3$, $R_4$, $R_5$, or $R_8$ is a linear or branched $C_9$-$C_{30}$ alkyl radical, if m or n is other than zero, then q is equal to 1, and if m or n is equal to zero, then p or q is equal to 0;

(ii) cetearyl alcohol, and (iii) at least one polyol with a molecular weight of greater than 80.

46. A cosmetic treatment process comprising applying a cosmetic composition to the hair, wherein the cosmetic composition comprises, in a cosmetically acceptable medium:
(i) at least one cationic poly(vinyllactam) polymer comprising:
  a) at least one monomer chosen from vinyllactam and alkylvinyllactam monomers;
  b) at least one monomer chosen from monomers of formulas (Ia) and (Ib):

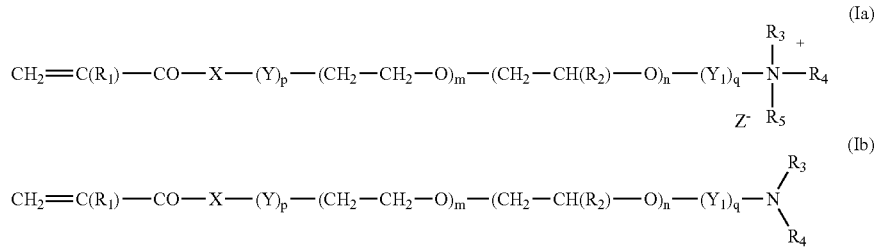

wherein:
X is chosen from oxygen and $NR_6$ radicals,
$R_1$ and $R_6$, which may be identical or different, are chosen from hydrogen and linear or branched $C_1$-$C_6$ alkyl radicals,
$R_2$ is chosen from linear or branched $C_1$-$C_4$ alkyl radicals,
$R_3$, $R_4$, and $R_5$, which may be identical or different, are chosen from hydrogen, linear or branched $C_1$-$C_{30}$ alkyl radicals, and radicals of formula (II):

$$-(Y_2)_r-(CH_2-CH(R_7)-O)_x-R_8 \quad (II)$$

Y, $Y_1$, and $Y_2$, which may be identical or different, are chosen from linear or branched $C_2$-$C_{16}$ alkylene radicals,
$R_7$ is chosen from hydrogen, linear or branched $C_1$-$C_4$ alkyl radicals, and linear or branched $C_1$-$C_4$ hydroxyalkyl radicals,
$R_8$ is chosen from hydrogen and linear or branched $C_1$-$C_{30}$ alkyl radicals,
p, q, and r, which may be identical or different, are equal to 0 or 1,
m and n, which may be identical or different, are chosen from integers ranging from 0 to 100,
x is an integer ranging from 1 to 100,
Z is an organic or mineral acid anion,
with the proviso that:
  at least one of the substituents $R_3$, $R_4$, $R_5$, or $R_8$ is a linear or branched $C_9$-$C_{30}$ alkyl radical,
  if m or n is other than zero, then q is equal to 1, and
  if m or n is equal to zero, then p or q is equal to 0;
(ii) cetearyl alcohol, and
(iii) at least one polyol with a molecular weight of greater than 80.

47. The cosmetic treatment process according to claim 46, wherein the application of the cosmetic composition is not followed by rinsing.

* * * * *

UNITED STATES PATENT AND TRADEMARK OFFICE
CERTIFICATE OF CORRECTION

| | |
|---|---|
| PATENT NO. | : 8,940,283 B2 |
| APPLICATION NO. | : 11/643861 |
| DATED | : January 27, 2015 |
| INVENTOR(S) | : Cecile Bebot |

It is certified that error appears in the above-identified patent and that said Letters Patent is hereby corrected as shown below:

In the Claims,

Column 45, line 25, "C1-C6" should be -- C1-C5 --.

Signed and Sealed this
Fifth Day of May, 2015

Michelle K. Lee
*Director of the United States Patent and Trademark Office*